(12) United States Patent
Pickford et al.

(10) Patent No.: US 7,939,076 B2
(45) Date of Patent: May 10, 2011

(54) METHODS FOR THE THERAPY OF INFLAMMATORY BOWEL DISEASE USING A TYPE-1 INTERFERON ANTAGONIST

(75) Inventors: Lesley B. Pickford, Menlo Park, CA (US); Christopher R. Bebbington, San Mateo, CA (US); Geoffrey T. Yarranton, Burlingame, CA (US); David King, Belmont, CA (US)

(73) Assignee: Medarex, Inc., Princeton, NJ (US)

( * ) Notice: Subject to any disclaimer, the term of this patent is extended or adjusted under 35 U.S.C. 154(b) by 0 days.

(21) Appl. No.: 10/831,432

(22) Filed: Apr. 23, 2004

(65) Prior Publication Data
US 2005/0152901 A1 Jul. 14, 2005

Related U.S. Application Data

(60) Provisional application No. 60/465,155, filed on Apr. 23, 2003.

(51) Int. Cl.
*A61K 39/395* (2006.01)
(52) U.S. Cl. .................. 424/144.1; 424/154.1
(58) Field of Classification Search .......... None
See application file for complete search history.

(56) References Cited

U.S. PATENT DOCUMENTS

| | | | |
|---|---|---|---|
| 4,816,567 A | 3/1989 | Cabilly et al. | |
| 5,516,515 A | 5/1996 | Vellucci et al. | |
| 5,693,762 A | 12/1997 | Queen et al. | |
| 5,731,169 A | 3/1998 | Mogensen et al. | |
| 5,861,258 A | 1/1999 | Mogensen et al. | |
| 5,886,153 A | 3/1999 | Mogensen et al. | |
| 5,889,151 A | 3/1999 | Mogensen et al. | |
| 5,919,453 A | 7/1999 | Benoit et al. | |
| 6,264,981 B1 | 7/2001 | Zhang et al. | |
| 6,458,932 B1 | 10/2002 | Novick et al. | |
| 6,713,609 B1 | 3/2004 | Chuntharapai et al. | |
| 6,787,634 B2 | 9/2004 | Benoit et al. | |
| 7,179,465 B2 | 2/2007 | Benoit et al. | |
| 7,285,526 B2 * | 10/2007 | Maroun | 514/2 |
| 7,465,451 B2 | 12/2008 | Benoit et al. | |
| 2002/0055492 A1 | 5/2002 | Benoit et al. | |
| 2003/0044410 A1 * | 3/2003 | Skurkovich et al. | 424/143.1 |
| 2003/0166228 A1 * | 9/2003 | Chuntharapai et al. | 435/199 |
| 2004/0067888 A1 | 4/2004 | Tovey et al. | |
| 2005/0152901 A1 | 7/2005 | Pickford et al. | |
| 2005/0208041 A1 | 9/2005 | Cardarelli et al. | |
| 2006/0029601 A1 | 2/2006 | Cardarelli et al. | |
| 2007/0014724 A1 * | 1/2007 | Witte et al. | 424/1.49 |

FOREIGN PATENT DOCUMENTS

| | | | |
|---|---|---|---|
| EP | 0369877 | | 5/1990 |
| EP | 0563487 A1 * | | 3/1993 |
| FR | 2 769 505 A1 | | 4/1999 |
| WO | WO 90/07861 | | 7/1990 |
| WO | WO 91/05862 | | 5/1991 |
| WO | WO 91/09967 | | 7/1991 |
| WO | WO 93/04699 | | 3/1993 |
| WO | WO-93/20187 A1 | | 10/1993 |
| WO | WO-94/14467 A1 | | 7/1994 |
| WO | WO-95/07716 A1 | | 3/1995 |
| WO | WO 95/13808 | | 5/1995 |
| WO | WO-97/41229 A1 | | 11/1997 |
| WO | WO 98/24884 | | 6/1998 |
| WO | WO 98/52976 | | 11/1998 |
| WO | WO 99/39211 | | 8/1999 |
| WO | WO 00/24417 | | 5/2000 |
| WO | WO 00/53635 | | 9/2000 |
| WO | WO 01/09187 | | 2/2001 |
| WO | WO 01/14424 | | 3/2001 |
| WO | WO 01/54721 | | 8/2001 |
| WO | WO-01/55215-AI | | 8/2001 |
| WO | WO 02/43478 | | 6/2002 |
| WO | WO 02/066649 | * | 8/2002 |
| WO | WO 2004/093908 | | 11/2004 |
| WO | WO 2004/094473 | | 11/2004 |

OTHER PUBLICATIONS

Huang et al., Pharmacol. Therapeut. 86: 201-215 (2000).*
Rampton et al., WJG 4(5): 369-376 (1998).*
Cohen, Curr. Gastroenter. Rep. 4: 497-505 (2002).*
Stewart et al., Cytokine Growth Factor Rev. Apr. 2003;14(2):139-54, ScienceDirect/Elsevier online publication of Feb. 21, 2003, numbered by the Examiner as pp. 1-31.*
Chuntharapai et al., Cytokine. Sep. 7, 2001;15(5):250-60.*
Merck Manual of Diagnosis and Therapy, Mark Beers and Robert Berkow, eds., Published by Merck Research Laboratories, 17th ed., 1999, pp. 302-313.*
Monteleone et al., Eur J Immunol. Aug. 2001;31(8):2247-55.*
Fais et al., J Interferon Res. Oct. 1994;14(5):235-8.*
Tanaguchi et al., Curr Opin Immunol. Feb. 2002;14(1):111-6.*
MacDonald et al., J Exp Med. Apr. 1, 1988;167(4):1341-9.*
Sollid et al., J Exp Med. Jan. 1, 1989;169(1):345-50.*
Lewerenz et al., J Mol Biol. Sep. 25, 1998;282(3):585-99.*
Musch et al., Aliment Pharmacol Ther. Jul. 2002;16(7):1233-9.*
Hanauer et al., Gastroenterology, (1994) vol. 106, No. 4 Suppl., pp. A696.*
Davidsen et al., Gastroenterology, (1994) vol. 106, No. 4 Suppl., pp. A670.*
Gasche et al., Gastroenterology, (1994) vol. 106, No. 4 Suppl., pp. A685.*
Biographical data for ATCC accession No. 65007, printed from the ATCC website on Jun. 4, 2010, pp. 1-2.*
GenBank accession No. J03171, Jun. 15, 1990, pp. 1-2.*
Benizri, E. et al.: "Prolonged Allograft Survival in Cynomolgus Monkeys Treated with a Monoclonal Antibody to the Human Type I Interferon Receptor and Lowdoses of Cyclosporine," Journal of Interferon and Cytokine Research, Mary Ann Liebert, Inc., New York, NY, US, vol. 18, 1998, pp. 273-284.

(Continued)

*Primary Examiner* — Zachary Skelding
(74) *Attorney, Agent, or Firm* — Baker Botts L.L.P.

(57) ABSTRACT

Compositions and methods for the therapy of Inflammatory Bowel Disease (IBD), including Celiac Disease, Crohn's Disease, and Ulcerative Colitis, are disclosed. Illustrative compositions comprise one or more anti-type 1 interferon antagonists, such as anti-type 1 interferon receptor antibody antagonists and fragments thereof, as well as polypeptides and small molecules that inhibit the interaction of type 1 interferon with its receptor (IFNAR).

16 Claims, 24 Drawing Sheets

OTHER PUBLICATIONS

Novick, D. et al.: "The Human Interferon Alpha/Beta Receptor: Characterization and Molecular Cloning" Cell, Cell Press, Cambridge, MA, US, vol. 77, No. 3, May 6, 1994.

Goldman, L. et al.: "Characterization of antihuman IFNAR-1 monoclonal antibodies: Epitope localization and functional analysis," Journal of Interferon and Cytokine Research, vol. 19, No. 1, Jan. 1999. pp. 15-26.

Novick, D. et al.:"The neutralization of type I IFN biologic actions bu anti-IFNAR-2 monoclonal antibodies is not entirely due to inhibition of Jak-Stat tyrosine phosphorylation," Journal of Interferon and Cytokine Research, vol. 20, No. 11, Nov. 2000, pp. 971-982.

Colamonici, O. et al.: "Characterization of three monoclonal antibodies that recognize the interferon alpha2 receptor," Proceedings of the National Academy of Sciences of USA, National Academy of Science, Washington, US, vol. 87, No. 18, Sep. 1990, pp. 7230-7234.

Constantinescu, S. et al.: "Role of interferon alpha/beta receptor chain 1 in the structure and transmembrane signaling of the interferon alpha/beta receptor complex," Proceedings of the National Academy of Sciences of USA, National Academy of Science, Washington, US, vol. 91, No. 20, Sep. 27, 1994, pp. 9602-9606.

Benoit, P. et al.:"A Monoclonal Antibody to Recombinant Human IFN-alpha Receptor Inhibits Biologic Activity of Several Species of Human IFN-alpha, IFN-beta, and IFN-Oniega. Detection of Heterogeneity of the Cellular Type I IFN Receptor," Journal of Immunology, The Williams and Wilkins Co., Baltimore, US, vol. 150, No. 3, Feb. 1, 1993, pp. 707-716.

Abramovich, C. et al.: "Human IFN-alpha Receptor Detected by Two Monoclonal Antibodies," Journal of Interferon Research, Mary Ann Liebert, Inc., New York, NY, US, vol. 12, No. suppl 1, Sep. 1, 1992, pp. S217.

Mitoro A, et al., "Exacerbation of ulcerative colitis during alpha-interferon therapy for chronic hepatitis C," Intern Med. (1993), 32(4):327-31.

Monteleone G, et al., "Role of interferon alpha in promoting T helper cell type 1 responses in the small intestine in coeliac disease," Gut. (2001), 48(3):425-9.

The New England Journal of Medicine, "Etanercept for Crohn's Disease", (2004) 350; 8, p. 840 Suzanne Travers and Thomas Kupper.

Sandborn et al., "Etanercept for Active Crohn's Disease: A Randomized, Double-Blind, Placebo-Controlled Trial", Gastroenterology (2001); 121:1088-1094.

Van den Brande et al., "Infliximab but not Etanercept Induces Apoptosis in Lamina Propria T-Lymphocytes From Patents With Crohn's Disease", Gastroenterology (2003); 124:1174-1785.

Nash and Florin, "Tumour Necrosis Factor Inhibitors", Medical Journal of Australia (2005); 183(4): 205-208.

U.S. Appl. No. 12/704,948, filed Feb. 12, 2010, Cardarelli et al.

Aguet et al., "Interferon 5" Ed. I. Gresser p. 1-22, Academic Press, London (1983).

Amin et al., "Innovations in Pharmaceutical Technology," Samedan Ltd, publishers, Jun. 2002.

Arvin AM and Miller JJ 3rd, "Acid labile α-interferon in sera and synovial fluids from patients with juvenile arthritis," Arthritis Rheum. (1984);27(5):582-5.

Barbas CF et al., "In vitro evolution of a neutralizing human antibody to human immunodeficiency virus type 1 to enhance affinity and broaden strain cross-reactivity," Proc Natl Acad Sci U S A. (1994);91(9):3809-13.

Blanco P, et al., "Induction of dendritic cell differentiation by IFN-α in systemic lupus erythematosus," Science. (2001);294(5546):1540-3.

Branca AA "Bovine spleen, a convenient source for purifying a type I interferon receptor," J. Interferon Res. 7(1):77-85 (1987).

Brinkmann V, et al., "Interferon α increases the frequency of interferon gamma-producing human CD4+ T cells," J Exp Med. (1993);178(5):1655-63.

Brown M, et al., "Tolerance of single, but not multiple, amino acid replacements in antibody VH CDR 2: a means of minimizing B cell wastage from somatic hypermutation?" J Immunol. (1996);156(9):3285-91.

Casset F, et al., "A peptide mimetic of an anti-CD4 monoclonal antibody by rational design," Biochem Biophys Res Commun. (2003);307(1):198-205.

Chen J, et al., "B cell development in mice that lack one or both immunoglobulin kappa light chain genes," EMBO J. (1993);12(3):821-30.

Chen C, et al., "Generation and analysis of random point mutations in an antibody CDR2 sequence: many mutated antibodies lose their ability to bind antigen," J Exp Med. (1992);176(3):855-66.

Colman PM, "Effects of amino acid sequence changes on antibody-antigen interactions," Res Immunol. (1994);145(1):33-6.

Cook JR, et al., "Differential responsiveness of a splice variant of the human type I interferon receptor to interferons," J Biol Chem. (1996);271(23):13448-53.

Corssmit EP, et al., "Effects of interferon-α (IFN-α) administration on leucocytes in healthy humans," Clin Exp Immunol. (1997);107(2):359-63.

Cutrone EC and Langer JA, "Identification of critical residues in bovine IFNAR-1 responsible for interferon binding," J Biol Chem. (2001);276(20):17140-8.

Debinski H, et al., "Low dose interferon gamma for refractory Crohn's disease," Ital J Gastroenterol Hepatol. (1997);29(5):403-6.

Deavin AJ, et al., "Statistical comparison of established T-cell epitope predictors against a large database of human and murine antigens," Mol Immunol. (1996);33(2):145-55.

Dunbar BS and Schwoebel ED, "Preparation of polyclonal antibodies," Methods in Enzymology (1990);182:663-70.

Eid P and Mogensen KE, "Purification of the alpha Interferon Receptor from Daudi cells," J. Interferon Res. (1987);7(6):762, Abstract No. I-22.

Eid P and Mogensen K, "Detergent extraction of the human α-β interferon receptor: a soluble form capable of binding interferon," Biochim Biophys Acta. (1990);1034(1):114-7.

Eid P and Tovey MG, "Characterization of a Domain of Human Type I Interferon Receptor Protein Involved in Ligand Binding", J. Interferon Cytokine Research, (1995);15:205-211.

Eid P, et al., "Localization of a receptor nonapeptide with a possible role in the binding of the type I interferons," Eur Cytokine Netw. (2000);11(4):560-73.

Epstein et al, "Direct evidence that the gene product of the human chromosome 21 locus, IFRC, is the interferon-α receptor," Biochemical and Biophysical Research Communications, (1982);107(3): 1060-1066.

Faltynek CR, et al., "Characterization of an interferon receptor on human lymphoblastoid cells," Proc Natl Acad Sci U S A. (1983);80(11):3269-73.

Filpula DR et al., "Structural and functional repetition in a marine mussel adhesive protein," Biotechnol Prog. (1990);6(3):171-7.

Finkelman FD, et al., "Regulation by interferon α of immunoglobulin isotype selection and lymphokine production in mice," J Exp Med. (1991);174(5):1179-88.

Fishwild DM, et al., "High-avidity human IgG kappa monoclonal antibodies from a novel strain of minilocus transgenic mice," Nat Biotechnol. (1996);14(7):845-51.

Folwaczny C, et al., "Crohn's disease: an immunodeficiency?" Eur J Gastroenterol Hepatol. (2003);15(6):621-6.

Foulis AK, et al., "Immunoreactive α-interferon in insulin-secreting β cells in type 1 diabetes mellitus," Lancet. (1987);2(8573):1423-7.

Gaboriaud C, et al., "Hydrophobic cluster analysis reveals duplication in the external structure of human α-interferon receptor and homology with gamma-interferon receptor external domain," FEBS Lett. (1990);269(1): 1-3.

Gahring LC, et al., "Antibodies prepared to neuronal glutamate receptor subunit3 bind IFN α-receptors: implications for an autoimmune process," Autoimmunity. 1998;28(4):243-8.

Geysen HM, et al., "Cognitive features of continuous antigenic determinants," J Mol Recognit. (1988);1(1):32-41.

Haller O, et al., "Virus-specific interferon action. Protection of newborn Mx carriers against lethal infection with influenza virus," J Exp Med. (1981);154(1):199-203.

Hardy MP, et al., "The soluble murine type I interferon receptor Ifnar-2 is present in serum, is independently regulated, and has both agonistic and antagonistic properties," Blood. (2001);97(2):473-82.

Harris WJ and Emery S, "Therapeutic antibodies—the coming of age," *Trends Biotechnol.* (1993);11(2):42-4.

Hertzog PJ, et al., "Interferons in rheumatoid arthritis: alterations in production and response related to disease activity," *Clin Immunol Immunopathol.* (1988);48(2):192-201.

Hooks JJ, et al., "Multiple interferons in the circulation of patients with systemic lupus erythematosus and vasculitis," *Arthritis Rheum.* (1982);25(4):396-400.

Hopkins SJ and Meager A. "Cytokines in synovial fluid: II. The presence of tumour necrosis factor and interferon," *Clin Exp Immunol.* (1988);73(1):88-92.

Janeway et al., *Immunobiology*, p. 3.2. Garland Science, New York, 1997.

Janeway et al., *Immunobiology*, 5th Ed., Garland Science, pp. 116-117 (2001).

Kettleborough, et al., "Humanization of a Mouse Monoclonal Antibody by CDR-grafting: the Importance of Framework Residues on Loop Conformation," *Protein Engineering* (1991); 4(7): 773-783.

Klimka et al., "Human anti-CD30 recombinant antibodies by guided phage antibody selection using cell panning," *Br J Cancer.* (2000);83(2):252-60.

Langer JA and Pestka S, "Interferon Receptors," *Immun. Today*, (1988);9(12):393-400.

Langer JA, et al., "Sublocalization on chromosome 21 of human interferon-α receptor gene and the gene for an interferon-gamma response protein," *Somat Cell Mol Genet.* (1990);16(3):231-40.

Langer JA. "Radiolabeling of the interferon-α receptor," *Biochem Biophys Res Commun.* (1988);157(3):1264-70.

Larrick et al, "Practical Aspects of Human Monoclonal Antibody Production," *Biotechniques*, pp. 6-14, Jan.-Feb. 1984.

Lederman S, et al., "A single amino acid substitution in a common African allele of the CD4 molecule ablates binding of the monoclonal antibody, OKT4," *Mol Immunol.* (1991);28(11):1171-81.

Li Y, et al., "The I binding specificity of human VH 4-34 (VH 4-21) encoded antibodies is determined by both VH framework region 1 and complementarity determining region 3," *J Mol Biol.* (1996);256(3):577-89.

Li CH, et al., "β-Endorphin omission analogs: dissociation of immunoreactivity from other biological activities," *Proc Natl Acad Sci U S A.* (1980);77(6):3211-4.

Lim JK and Langer JA "Generation and characterization of anti-idiotypic antibodies recognizing the interferon-alpha receptor: implications for ligand-receptor interactions," *J Interferon Res.* Aug. 1993;13(4):295-301.

Lindenmann J, "Induction of chick interferon: procedures of the original experiments," *Methods Enzymol.* 1981;78(Pt A):181-8.

Lonberg N, et al., "Antigen-specific human antibodies from mice comprising four distinct genetic modifications," *Nature.* (1994);368(6474):856-9.

Lu J, et al., "Structure-function study of the extracellular domain of the human IFN-α receptor (hIFNAR1) using blocking monoclonal antibodies: the role of domains 1 and 2," *J Immunol.* (1998);160(4):1782-8.

Luft T, et al., "Type I IFNs enhance the terminal differentiation of dendritic cells," *J Immunol.* (1998);161(4):1947-53.

Luft T, et al., "IFN-α enhances CD40 ligand-mediated activation of immature monocyte-derived dendritic cells," *Int Immunol.* (2002);14(4):367-80.

Lutfalla G, et al., "The structure of the human interferon α/β receptor gene," *J Biol Chem.* (1992);267(4):2802-9.

MacCallum RM, et al., "Antibody-antigen interactions: contact analysis and binding site topography," *J Mol Biol.* (1996);262(5):732-45.

Madsen SM, et al., "An open-labeled, randomized study comparing systemic interferon-alpha-2A and prednisolone enemas in the treatment of left-sided ulcerative colitis," *Am J Gastroenterol.* (2001); 96(6): 1807-15.

Marks et al., "By-passing immunization: building high affinity human antibodies by chain shuffling," *Biotechnology* (N Y). (1992);10(7):779-83.

Martin T, et al., "Structure-function studies on a polyreactive (natural) autoantibody. Polyreactivity is dependent on somatically generated sequences in the third complementarity-determining region of the antibody heavy chain," *J Immunol.* (1994);152(12):5988-96.

Mateo C, et al., "Removal of amphipathic epitopes from genetically engineered antibodies: production of modified immunoglobulins with reduced immunogenicity," *Hybridoma.* (2000);19(6):463-71.

Mayo MS, et al., "B lymphocyte migration to the bone marrow of humans is not random," *Stat Med.* (1999);18(2):223-31.

Meadows et al, "Partial Purification of the Human Receptor for Interferon-alpha (IFN-α)," *J. Interferon Res.* (1990);10(Suppl. 1):5159, Abstract No. II8-8.

Meadows LM and Ozer H, "Purification of the Putative Receptor for Interferon-alpha (IFN-α)," *Proc. Am. Assoc. Cancer Res.* (1990);31:55, Abstract No. 328.

Miller JJ 3rd, et al., "VH4-34 (VH4.21) gene expression in the chronic arthritides of childhood: studies of associations with antilipid A antibodies, HLA antigens, and clinical features," *J Rheumatol.* (1996);23(12):2132-9.

Mogensen, et al., "The Type I Interferon Receptor: Structure, Function and Evolution of a Family Business," *J. of Interferon and Cytokine Research* (1999);19:1069-1098.

Mouchel-Vielh E, et al., "Specific antiviral activities of the human α interferons are determined at the level of receptor (IFNAR) structure," *FEBS Lett.* (1992);313(3):255-9.

Nikolaus S, et al., "Interferon beta-1a in ulcerative colitis: a placebo controlled, randomised, dose escalating study," *Gut.* (2003);52(9):1286-90.

O'Brien et al., "Humanizatino of Monoclonal Antibodies by CDR Grafting," *Methods in Molecular Biology*, Humana Press, (2003):81-100.

Ohlin M and Borrebaeck CA, "Characteristics of human antibody repertoires following active immune responses in vivo," *Mol Immunol.* (1996);33(7-8):583-92.

Paul, *Fundamental Immunology*, 3rd Ed., pp. 292-295, Raven Press, New York, 1993.

Platanias and Colamonici, "Interferon alpha Induces Rapid Tyrosine Phosphorylation of the a Subunit of Its Receptor," *The Journal of Biological Chemistry*, (1992);267(33):24053-24057.

Pritsch O, et al., "VH gene usage by family members affected with chronic lymphocytic leukaemia," *Br J Haematol.* (1999);107(3):616-24.

Rader et al., "A phage display approach for rapid antibody humanization: designed combinatorial V gene libraries," *Proc Natl Acad Sci U S A.* (1998);95(15):8910-5.

Radvanyi LG, et al., "Low levels of interferon-α induce CD86 (B7.2) expression and accelerates dendritic cell maturation from human peripheral blood mononuclear cells," *Scand J Immunol.* (1999);50(5):499-509.

Raziuddin et al, "Receptors for human α and β interferon but not for gamma interferon are specified by human chromosome 21," *Proceedings National Academy Science*, (1984);81:5504-5508.

Reff ME and Heard C, "A review of modifications to recombinant antibodies: attempt to increase efficacy in oncology applications," *Crit Rev Oncol Hematol.* (2001);40(1):25-35.

Revel et al, "Interferon receptor and interferon-activated genes," *ICSU Short Reports*, (1986);4:362-365.

Riechmann L, et al., "Reshaping human antibodies for therapy," *Nature.* (1988);332(6162):323-7.

Rudikoff S, et al., "Single amino acid substitution altering antigen-binding specificity," *Proc Natl Acad Sci U S A.* (1982);79(6):1979-83.

Santini SM, et al., "Type I interferon as a powerful adjuvant for monocyte-derived dendritic cell development and activity in vitro and in Hu-PBL-SCID mice," *J Exp Med.* (2000);191(10):1777-88.

Schellekens H, et al., "Factors inhibiting IFN activity," *Biotherapy.* 1996;8(3-4):199-204.

Shearer M and Taylor-Papadimitriou, "Interferon Receptor Interaction: A Study Using Monoclonal Antibodies to HuIFNα," *J. Cell. Biochem.* Supple. (12 Part A):216 (1988).

Scott MG, et al., "Clonal characterization of the human IgG antibody repertoire to Haemophilus influenzae type b polysaccharide. IV. The less frequently expressed VL are heterogeneous," *J Immunol.* (1991);147(11):4007-13.

Short MK, et al., "A single H:CDR3 residue in the anti-digoxin antibody 26-10 modulates specificity for C16-substituted digoxin analogs," *Protein Eng.* (2001);14(4):287-96.

Siemers R, "Interferon alpha receptor from bovine spleen: Evidence of two molecular weight forms," *Pro. Am. Assoc. Cancer Res.* (1990);31:238, Abstract No. 1410.

Soderlind et al., "The immune diversity in a test tube—non-immunised-antibody libraries and functional variability in defined protein scaffolds," *Comb Chem High Throughput Screen.* (2001);4(5):409-16.

Shulman L et al, "Molecular cloning of the human IFN-α, β receptor cDNA." *J. Interferon Res.* (1988);8(1):S16, abstract No. 3-9.

Streuli M, et al., "Target cell specificity of two species of human interferon-α produced in *Escherichia coli* and of hybrid molecules derived from them," *Proc Natl Acad Sci USA.* (1981);78(5):2848-52.

Sümer N and Palabiyikoğlu M, "Induction of remission by interferon-alpha in patients with chronic active ulcerative colitis," *Eur J Gastroenterol Hepatol.* (1995);7(7):597-602.

Tilg H, et al., "A randomised placebo controlled trial of pegylated interferon alpha in active ulcerative colitis," *Gut.* (2003);52(12):1728-33.

Tilg H, et al., "Interferon-α induces circulating tumor necrosis factor receptor p55 in humans," *Blood.* (1995);85(2):433-5.

Tough DF, et al., "Induction of bystander T cell proliferation by viruses and type I interferon in vivo," *Science.* (1996);272(5270):1947-50.

Traub A, et al., "Purification and properties of the α-interferon receptor of human lymphoblastoid (Namalva) cells," *J Biol Chem.* (1984);259(22):13872-7.

UniProt Accession No. P17181, INAR1_Human, Dec. 12, 2006.

Uzé G, et al., "Behavior of a cloned murine interferon α/β receptor expressed in homospecific or heterospecific background," *Proc Natl Acad Sci USA.* (1992);89(10):4774-8.

Uzé et al., "Murine Tumor Cells Expressing the Gene for the Human Interferon αβ Receptor Elicit Antibodies in Syngeneic Mice to the Active Form of the Receptor," *Eur. J. Immunol* (1991);21:447-451.

Uzé G, et al., "Genetic transfer of a functional human interferon a receptor into mouse cells: cloning and expression of its cDNA," *Cell.* (1990);60(2):225-34.

Vajdos FF, et al., "Comprehensive functional maps of the antigen-binding site of an anti-ErbB2 antibody obtained with shotgun scanning mutagenesis," *J Mol Biol.* (2002);320(2):415-28.

Waldrnann TA, "Monoclonal antibodies in diagnosis and therapy," *Science.* (1991);252(5013):1657-62.

Winter G and Harris WJ, "Humanized antibodies," *Trends Pharmacol Sci.* (1993);14(5):139-43.

Wu et al., "Stepwise in vitro affinity maturation of Vitaxin, an αv β3-specific humanized mAb," *Proc Natl Acad Sci U S A.* (1998);95(11):6037-42.

Wu H, et al., "Humanization of a murine monoclonal antibody by simultaneous optimization of framework and CDR residues," *J Mol Biol.* (1999);294(1):151-62.

Xu J et al., "A genomic view of the human-Bacteroides thetaiotaomicron symbiosis," *Science.* (2003);299(5615):2074-6.

Yang et al., "CDR walking mutagenesis for the affinity maturation of a potent human anti-HIV-1 antibody into the picomolar range," *J Mol Biol.* (1995);254(3):392-403.

Yonehara et al., "Monoclonal Anti-Idiotype Antibody for Anti-Human Interferon-α that complete with Interferon-α in Binding to Human Cell Surface and Inhibit the Interferon Action," *Elsevier Sci. Publ. BV,* (1986), pp. 167-171.

Ruther U et al., "Interferon Alpha (IFN Alpha 2a) Therapy for herpes virus-associated inflammatory bowel disease (ulcerative colitis and Crohn's disease)," *Hepatogastroenterology* (1998);45(21):691-9.

Tovey, M. et al., "Mucosal Cytokine Therapy: Marked Antiviral and Antitumor Activity," Journal of Interferon and Cytokine Research (1999);19(8):911-921.

von Andrian U. H. & Engelhardt B, "α4 Integrins as Therapeutic Targets in Autoimmune Disease," N Engl J Med (2003); 348:68-72.

\* cited by examiner

Phase II Mean Hyperplasia Score

Phase II Mean Hyperplasia Score % Change

FIG. 14A

H3 – heavy chain variable region of CPI-1697

EVQLVESGGGLVQPGGSLRLSCAFSGFTLSTSGMGIGWVRQAPGKGLEWVA
HVWWDDDKYYNPSLKSRFTISRDTSKNTVYLQMNSLRAEDTAVYYCAR
NYYPYDAWFDYWGQGTLVTVS

FIG. 14B

K1 – light chain variable region of CPI-1697

DIQMTQSPSSLSASVGDRVTITCSASSSINSNHLHWYQQKPGKAPKLLIYRTSILASGVPSRF
SGSGSGTSFTLTISSLQPEDFATYYCQQGSNIPFTFGQGTKVEIKR

METHODS FOR THE THERAPY OF INFLAMMATORY BOWEL DISEASE USING A TYPE-1 INTERFERON ANTAGONIST

CROSS REFERENCE TO RELATED APPLICATION

This application claims the benefit of the filing date of U.S. Ser. No. 60/465,155, filed Apr. 23, 2003, the entire contents of which are incorporated herein by reference.

BACKGROUND OF THE INVENTION

1. Technical Field of the Invention

The present invention relates generally to the therapy of Celiac Disease, Crohn's Disease, and Ulcerative Colitis (collectively referred to as Inflammatory Bowel Disease, or IBD). The invention is more specifically related to antagonists of type-1 interferon as well as to therapeutic methods employing such antagonists for the treatment of IBD.

2. Description of Related Art

Celiac Disease, Crohn's Disease, and Ulcerative Colitis (collectively referred to as Inflammatory Bowel Disease, or IBD) are chronic, inflammatory diseases of the gastrointestinal tract. While the clinical features vary somewhat between these two disorders, both are characterized by abdominal pain, diarrhea (often bloody), a variable group of 'extra-intestinal' manifestations (such as arthritis, uveitis, skin changes, etc) and the accumulation of inflammatory cells within the small intestine and colon (observed in pathologic biopsy or surgical specimens).

IBD affects both children and adults, and has a bimodal age distribution (one peak around 20, and a second around 40). IBD is a chronic, lifelong disease, and is often grouped with other so-called "autoimmune" disorders (e.g. rheumatoid arthritis, type I diabetes mellitus, multiple sclerosis, etc). IBD is found almost exclusively in the industrialized world. The most recent data from the Mayo Clinic suggest an overall incidence of greater than 1 in 100,000 people in the United States, with prevalence data in some studies greater than 1 in 1000. There is a clear trend towards an increasing incidence of IBD in the US and Europe, particularly Crohn's Disease. The basis for this increase is not presently clear. As such, IBD represents the $2^{nd}$ most common autoimmune disease in the United States (after rheumatoid arthritis).

Type 1 interferons have been detected in the gut of patients with Inflammatory Bowel Disease. For example, interferon alpha was reported to be overexpressed in the gut mucosa of patients with Celiac Disease, a gluten-sensitive enteropathy, and in the lamina propria of Crohn's Disease patients. Monteleone et al., Gut 48:425-429 (2001); Fais et al., J. Interferon Res. 14:235-238 (1994). The biological significance of the type 1 interferons in the tissues from these disease patients has not been described. Type 1 interferons have not been described in the circulation of individuals with Inflammatory Bowel Disease and it is unclear what role, if any, interferon alpha plays in the pathology of these diseases.

Type 1 interferons (i.e. interferons alpha and beta) are multifunctional cytokines that play a critical role in a variety of immune response systems. Abnormal production of type 1 interferons is associated with several pathological conditions including transplant rejection and autoimmune diseases such as rheumatoid arthritis, systemic lupus erythematosus, and insulin dependent diabetes. The biological effects of type 1 interferons are mediated through a single cell-surface receptor (IFNAR) that binds to all of the type 1 interferons but not to the type 2 interferon, interferon-γ. The type 1 interferon receptor is expressed at varying levels on all nucleated cells in the body. It is composed of two polypeptide chains designated IFNAR1 and IFNAR2, that, together, constitute the high-affinity receptor capable of transducing an intracellular signal upon interferon binding.

A mouse monoclonal antibody, designated 64G12, directed against the IFNAR1 chain of the human type 1 interferon receptor, has been shown to block the activity of type 1 interferons by interfering with the binding of the cytokines to their receptor. (See, U.S. Pat. Nos. 5,889,151, 5,886,153, 5,731,169, 5,861,258, and 5,919,453, and 6,475,983, as well as U.S. Patent Application Publication No. 20020055492, each of which is incorporated by reference herein in its entirety). In primate transplantation models, 64G12, given in conjunction with cyclosporine, has provided remarkable long-term efficacy in prevention of skin allograft rejection and graft-versus host disease. Benizri et al., J. Interferon Cytokine Res. 18:273 (1998).

Treatment of IBD is varied. First line therapy typically includes salicylate derivatives (e.g., 5-ASA) given orally or rectally. Response rates in uncomplicated Crohn's Disease are approximately 40% (compared to 20% for placebo). Corticosteroids remain a mainstay in the treatment of patients with more "refractory" disease, despite the untoward side-effects. Newer treatment options include anti-metabolites (e.g., methotrexate, 6-mercaptopurine) and immunomodulators (e.g., Remicade—a chimeric human antibody directed at the TNFα receptor).

In spite of considerable research into therapies for these disorders, Celiac Disease, Crohn's disease and ulcerative cholitis remain difficult to treat effectively. Accordingly, there remains an unmet need in the art for improved methods for treating such Inflammatory Bowel Diseases. The present invention fulfills these and other related needs.

SUMMARY OF THE INVENTION

The present invention provides compositions and methods for the treatment of Inflammatory Bowel Disease, including, for example Celiac Disease, Crohn's disease and ulcerative colitis. Compositions of the present invention comprise one or more type 1 interferon antagonist, such as, for example, anti-type 1 interferon antibodies, anti-IFNAR antibodies, fragments of any of the aforementioned antibodies, proteins and small molecules. Within some embodiments, antagonists according to the present invention may be chimeric, primatized, humanized, de-immunized and/or human antibodies or receptor binding fragment thereof. Within other embodiments, the present invention provides therapeutic methods comprising the step of administering to a patient afflicted with IBD, a therapeutically effective amount of a type 1 interferon antagonist. Still further embodiments provide therapeutic methods comprising the steps of (a) administering to a patient afflicted with IBD, a tolerizing amount of a type 1 interferon antagonist and (b) administering to the patient a therapeutically effective amount of a type 1 interferon antagonist.

Thus, within certain embodiments of the present invention are provided antagonists that interfere with type 1 interferon ligand binding such as, for example, soluble receptor chains (e.g. soluble IFNAR2). Other related embodiments provide antibodies or antigen binding fragments thereof that selectively bind to one or more type 1 interferon or bind to the IFNAR receptor in such a way that they interfere with ligand binding, such as, for example, by competitive, non-competitive or uncompetitive inhibition. Alternative embodiments provide antagonists that interfere with signal transduction by the IFNAR receptor. Still further embodiments provide antagonists that antagonize the downstream effects of type 1 interferons.

Suitable antibody antagonists for use in the therapeutic methods of the present invention include monoclonal antibodies such as, for example, non-human, chimeric, primatized, humanized, de-immunized and/or fully human antibodies or antigen binding fragments thereof. Antibody antagonists may further comprise one or more chemical modifications to increase the antibody's, or antigen binding fragment thereof, half-life in circulation such as, for example, crosslinking to polyethylene glycol (i.e. PEGylation).

Within certain preferred embodiments, the antagonist is an antibody that binds at or near the IFNAR1 antigenic epitope recognized by the murine monoclonal antibody designated 64G12 and/or the engineered human variant designated CPI-1697. The 64G12 monoclonal antibody was deposited at the ECACC (European Collection of Animal Cell Cultures Porton Down Salisbury, Wiltshire SP4 056, United Kingdom) on Feb. 26, 1992.

Further embodiments of the present invention further comprise one or more additional therapeutic such as, for example, an immunosuppressive, an anti-inflammatory, a steroid, an immunomodulatory agent, a cytokine, and a TNF antagonist. Exemplary immunosuppressives include azathioprine, methotrexate, cyclosporine, FK506, rapamycin, and mycophenolate mofetil. Exemplary anti-inflammatories include 5-aminosalicylic acid, sulfasalazine and olsalazine. Exemplary steroids include corticosteroids, glucocorticosteroids, prednisone, prednisolone, hydrocortisone, methylprednisolone, dexamethasone and ACTH. Exemplary immunomodulatory agents include PVAC, anti-CD40 ligand, anti-CD40, natalizumab (Antegren™), anti-VCAM1 and anti-ICAM1. Exemplary cytokines include IL-10. Exemplary TNF antagonists include infliximab (Remicade®), etanercept (Enbrel®), adalimumab (Humira™), and CDP870.

By other embodiments of the present invention are provided methods for the treatment of an Inflammatory Bowel Disease such as, for example, Celiac Disease, Crohn's Disease, and ulcerative colitis which methods comprise the step of administering to a patient afflicted with an Inflammatory Bowel Disease a therapeutically effective amount of a type 1 interferon antagonist as disclosed herein above.

By the methods of the present invention, the antagonist may be administered by any suitable route of delivery so as to ensure appropriate bioavailability. Thus, within certain embodiments, suitable routes of administration may include intravenous bolus, intravenous slow bolus, or infusion. By other embodiments, administration of the type 1 interferon antagonist may be achieved through subcutaneous, intramuscular, transdermal or intradermal injection. Alternative embodiments provide that administration may be achieved through mucosal delivery such as, for example, through inhalation, or through nasopharyngeal or oral administration.

Within certain embodiments employing a protein antagonist, such as, for example, an antibody and/or an antigen binding fragment thereof, the route of administration may be subcutaneous, intramuscular and/or intravenous. Intravenous administration may be as a bolus injection, a slow bolus injection or as an infusion. Alternative embodiments provide that the protein antagonists may be delivered transdermally, intradermally, and mucosally.

Exemplary dosages may be between 0.1 and 50 mg/kg body weight, inclusive, more preferably between 0.5 and 10 mg/kg body weight, inclusive, and still more preferably between 2 and 5 mg/kg, inclusive. Within certain embodiments, multiple repeat doses may be administered.

Within embodiments of the present invention employing protein antagonists, the dosing frequency may be in the range of once per day to once per month, inclusive, more preferably, in the range of twice per week to every two weeks, inclusive, and still more preferably approximately once per week. Alternatively, the antagonist may be dosed at approximately the in vivo half-life if provided adequate exposure.

Certain other embodiments of the present invention provide that the antagonist may be administered in combination with other therapeutics such as, for example, an immunosuppressive, an anti-inflammatory, a steroid, an immunomodulatory agent, a cytokine, and a TNF antagonist such as those identified herein above.

Still further embodiments of the present invention provide methods for treating a patient suffering from an Inflammatory Bowel Disease which methods comprise the steps of (a) administering a tolerizing dose of a protein-based type 1 interferon antagonist and (b) administering a therapeutically effective dose of said protein-based type 1 interferon antagonist. Within preferred embodiments of these methods, the interferon antagonist may be an antibody against the type 1 interferon receptor (IFNAR). Exemplary anti-type 1 interferon antibodies include chimeric, primatized, humanized, de-immunized and human antibodies. Certain preferred anti-IFNAR antibodies include those that bind to IFNAR1 such as, for example, the murine monoclonal antibody designated 64G12 and/or the engineered human variant designated CPI-1697.

Preferred ranges for the tolerizing dose of the protein-based type 1 interferon antagonist are between 10 mg/kg body weight to 50 mg/kg body weight, inclusive. More preferred ranges for the tolerizing dose are between 20 mg/kg body weight and 40 mg/kg body weight, inclusive. Still more preferred ranges for the tolerizing dose are between 20 and 25 mg/kg body weight, inclusive.

Within these therapeutic regimens, the therapeutically effective dose of anti-type 1 interferon is preferably administered in the range of 0.1 to 10 mg/kg body weight, inclusive. More preferred therapeutically effective doses are in the range of 0.2 to 5 mg/kg body weight, inclusive. Still more preferred therapeutically effective doses are in the range of 0.5 to 2 mg/kg body weight, inclusive. Within alternative embodiments, the subsequent therapeutic dose or doses may be in the same or different formulation as the tolerizing dose and/or may be administered by the same or different route as the tolerizing dose. Preferably the therapeutic doses are administered intravenously, intramuscularly, or subcutaneously.

BRIEF DESCRIPTION OF THE DRAWINGS

FIGS. 1A-1D show results for Phase I studies. FIGS. 2A-2D show results for Phase II studies. Percent body weight change of each animal was calculated using its body weight on Day 0, the dosing initiation day as the baseline. Percent individual and group mean body weight changes and group mean body weights of surviving animals were plotted. Statistical analyses (one way ANOVA) were performed for all time points for the treated and control groups. **: At Week 55 of Phase I study, treated animals had statistically significant body weight changes compared with the controls ($p<0.01$). Arrows represent the dosing schedules.

FIGS. 3A-3D show results for Phase I studies. FIGS. 4A-4D show results for Phase II studies. Weekly average diarrhea scores (average of five week days) of surviving animal were plotted for the control and treated groups. Group mean weekly average diarrhea scores and percent group mean weekly diarrhea score change with Week-1, right before the dosing initiation as the baseline, were also plotted. Arrows represent the dosing schedules.

FIGS. 5A-5D show results for Phase I studies. FIGS. 6A-6D show results for Phase II studies. Activity scores representing neutrophil infiltration (average of three biopsy samples) of surviving animal were plotted for the control and treated groups. Group mean activity scores and percent group mean weekly activity score change with Week-1 for Phase I and Week-2 for Phase II, before the dosing initiation as the baseline, were also plotted. Arrows represent the dosing schedules.

FIGS. 7A-7D show results for Phase I studies. FIGS. 8A-8D show results for Phase II studies. Chronicity scores representing extent of permanent changes to the colon morphology, including loss of crypts and alterations in glandular structures (average of three biopsy samples) of surviving animal were plotted for the control and treated groups. Group mean activity scores and percent group mean weekly chronicity score change with Week-1 for Phase I and Week-2 for Phase II, before the dosing initiation as the baseline, were also plotted. Arrows represent the dosing schedules.

FIGS. 9A-9D show results for Phase I studies. FIGS. 10A-10D show results for Phase II studies. Hyperplasia scores representing abnormal increase in mucosal tissue thickness, including cellular and interstitial tissue (average of three biopsy samples) of surviving animal were plotted for the control and treated groups. Group mean activity scores and percent group mean weekly hyperplasia score change with Week-1 for Phase I and Week-2 for Phase II, before the dosing initiation as the baseline, were also plotted. Arrows represent the dosing schedules.

FIGS. 14A-14B (SEQ ID NOS:1-2) show the amino acid sequences of the heavy chain (H3) (FIG. 14A) (SEQ ID NO: 1) and light chain (K1) (FIG. 14B) (SEQ ID NO:2) of the humanized anti-IFNAR-1 antibody CPI-1697. The CDRs are underlined.

DETAILED DESCRIPTION OF THE INVENTION

Figure 1A:
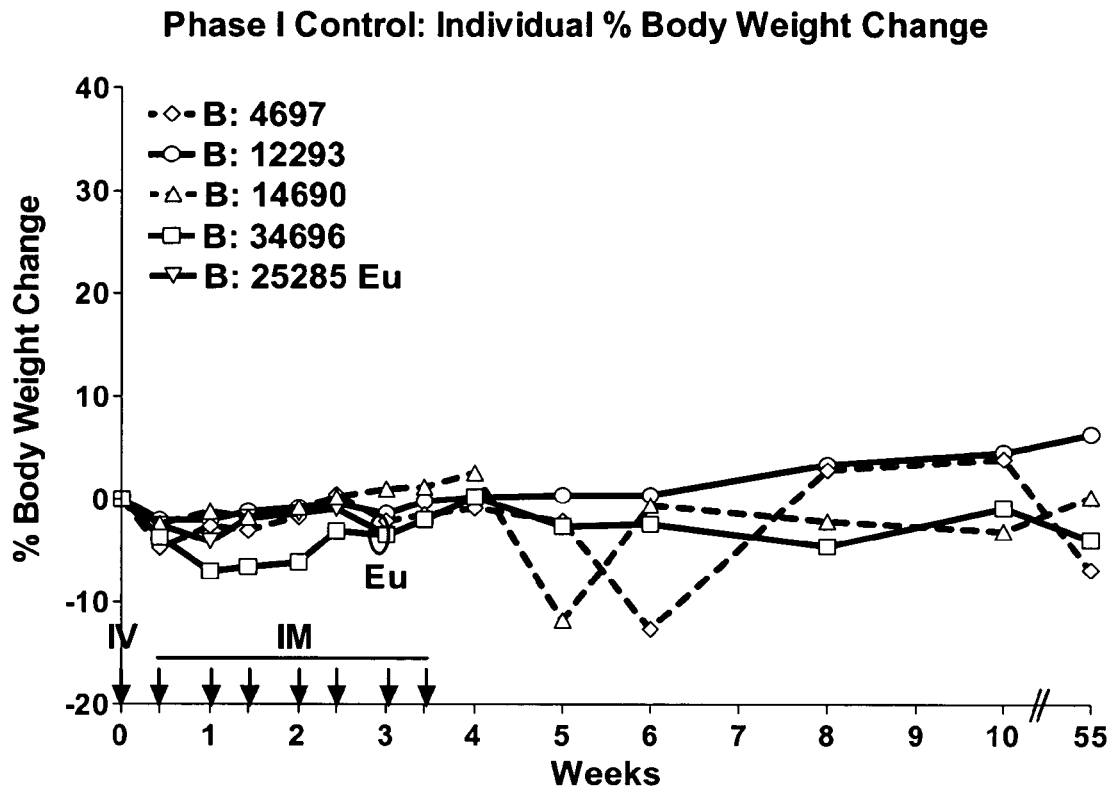
FIGS. 1A-1D and 2A-2D are graphs showing the effect of CPI-1697 on body weights of IBD-afflicted CTT.
Figure 1B:
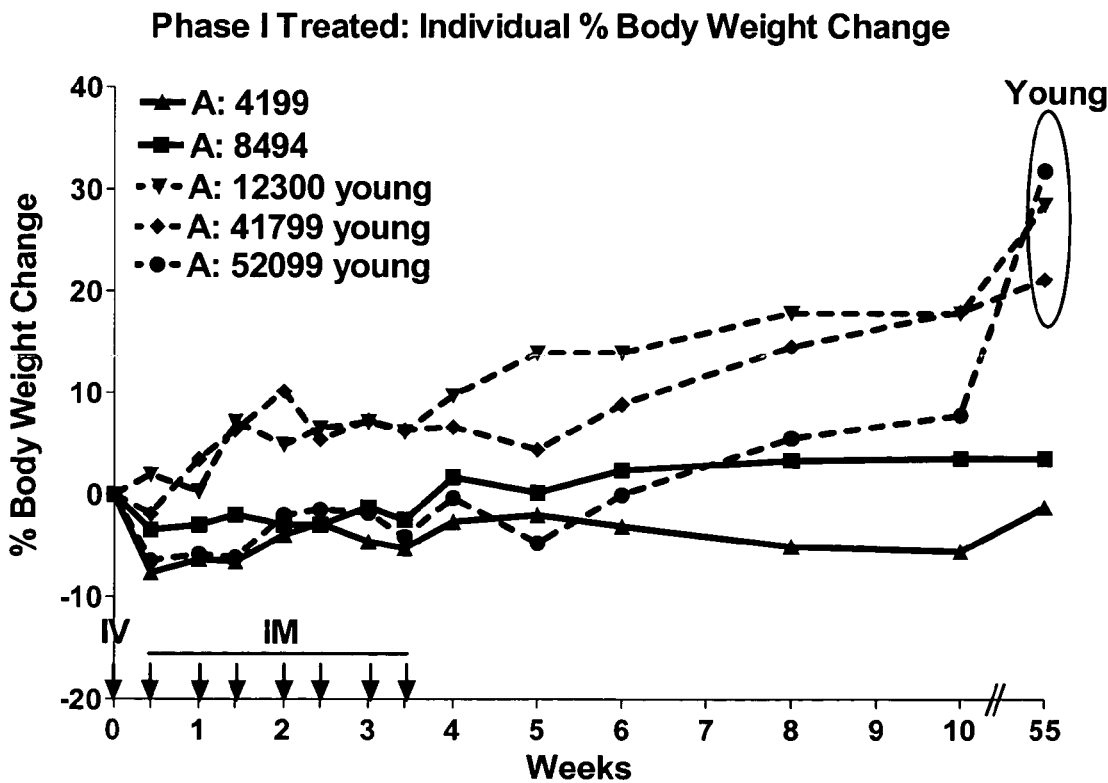
Figure 1C:
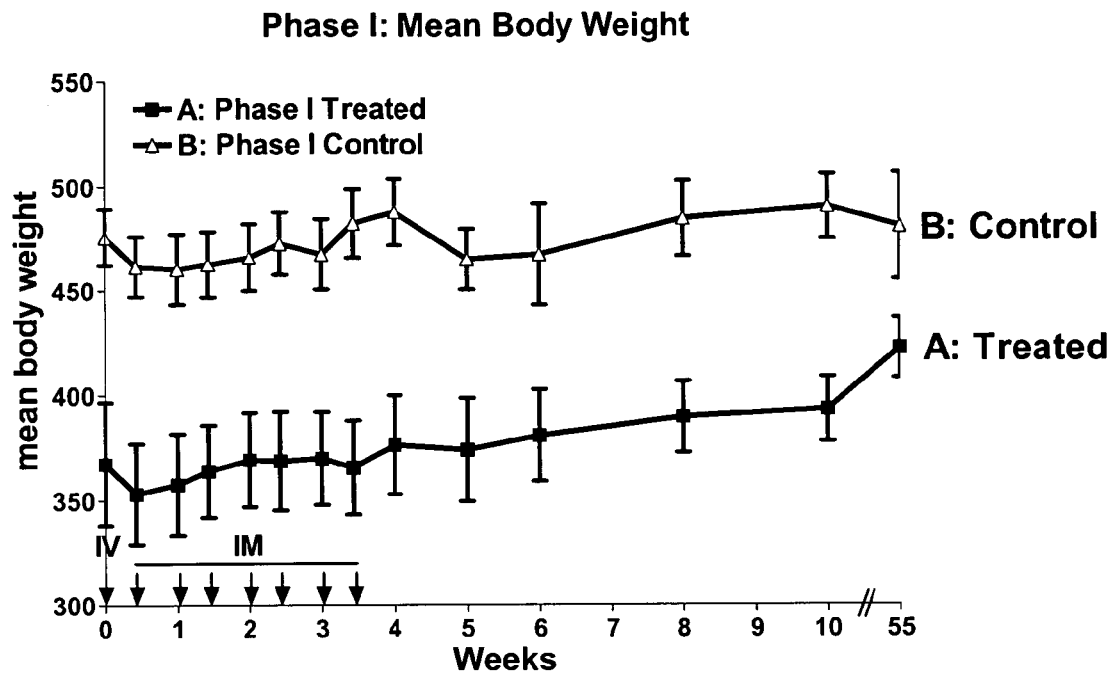
Figure 1D:
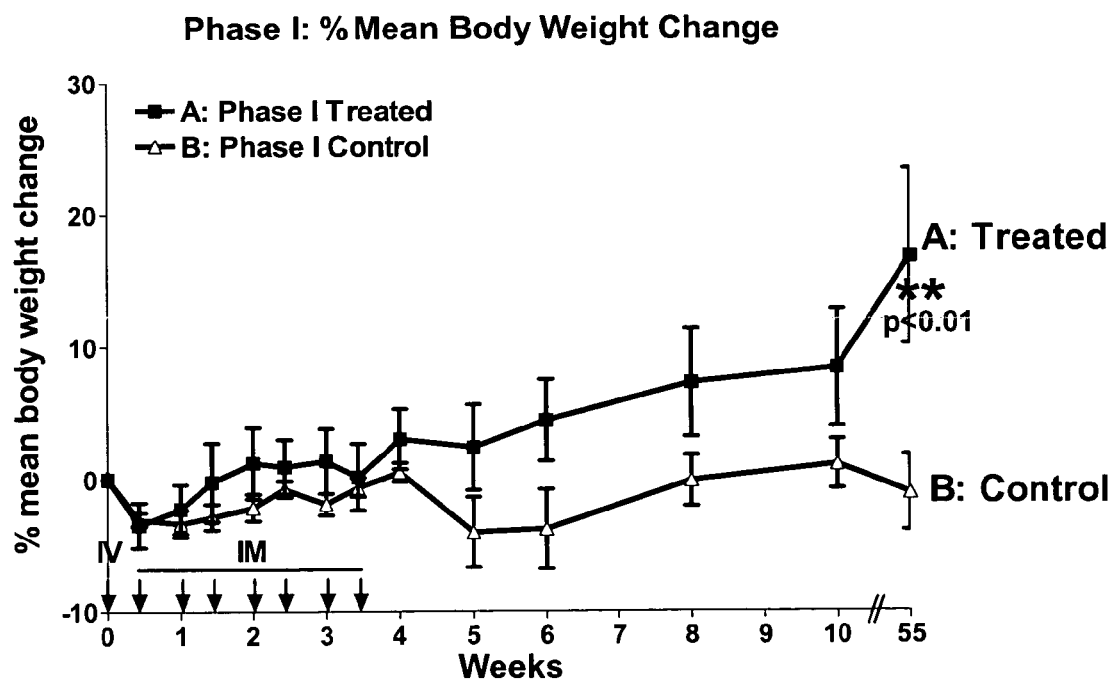
Figure 2A:
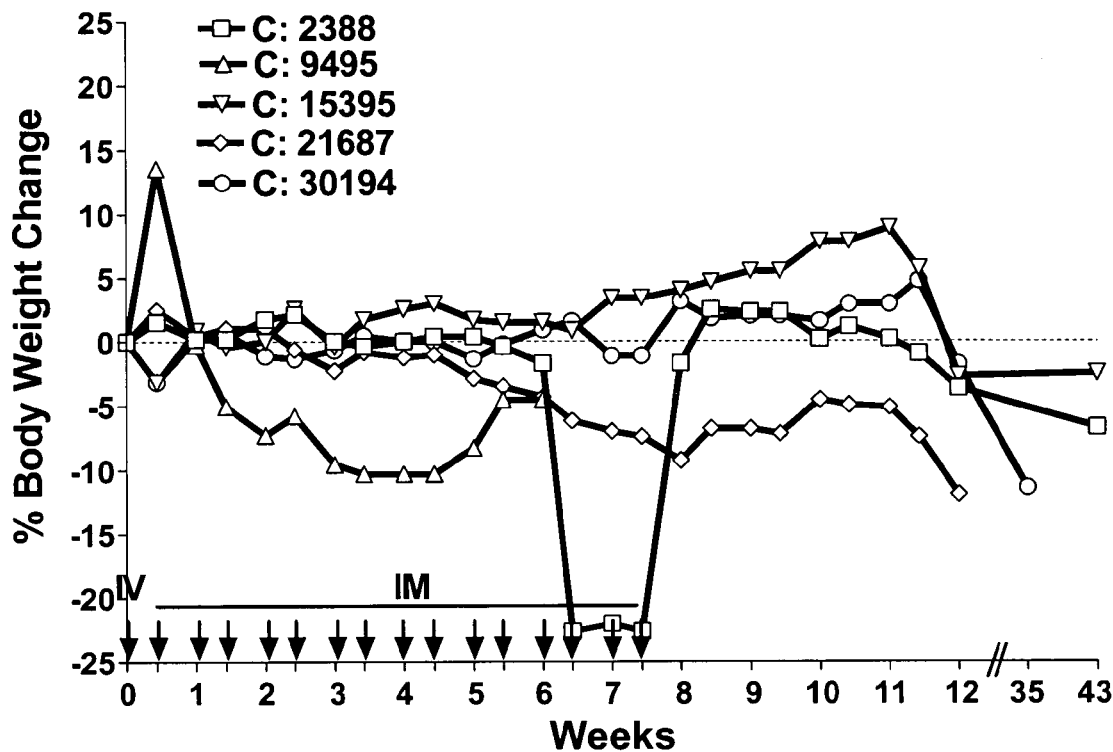
Figure 2B:
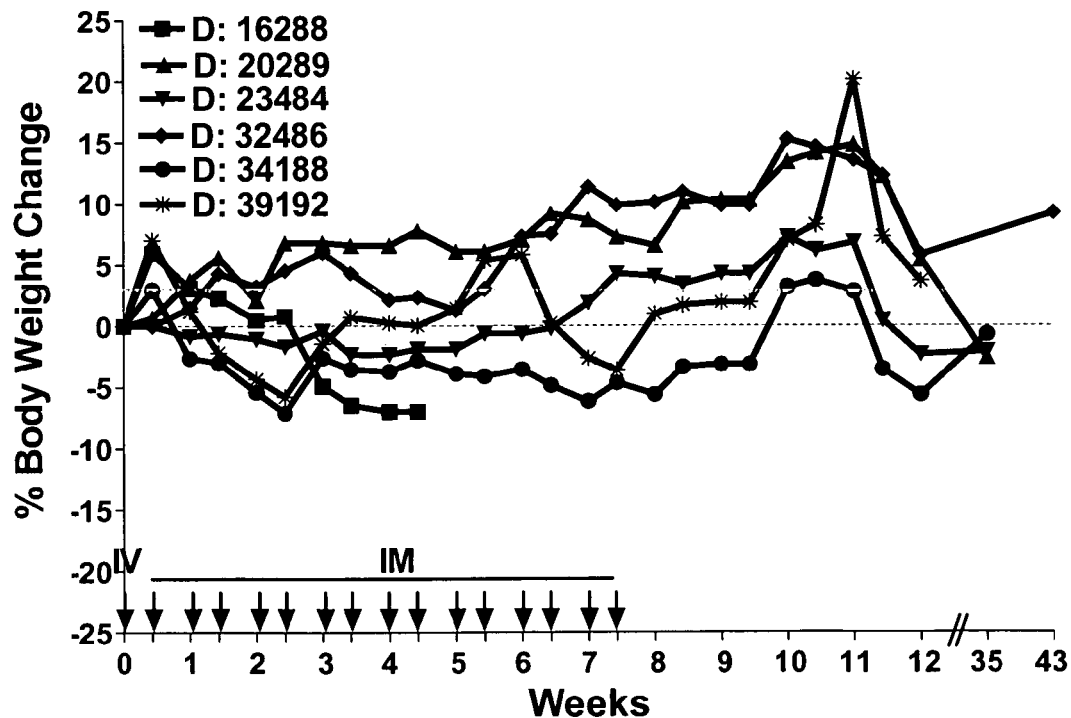
Figure 2C:
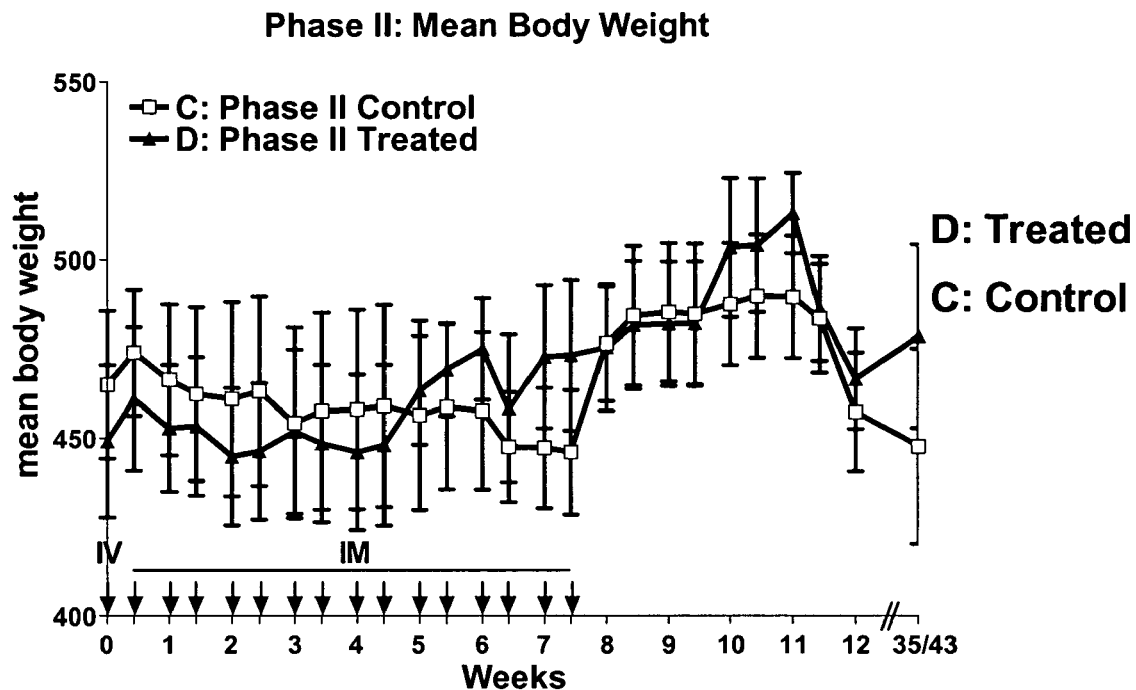
Figure 2D:
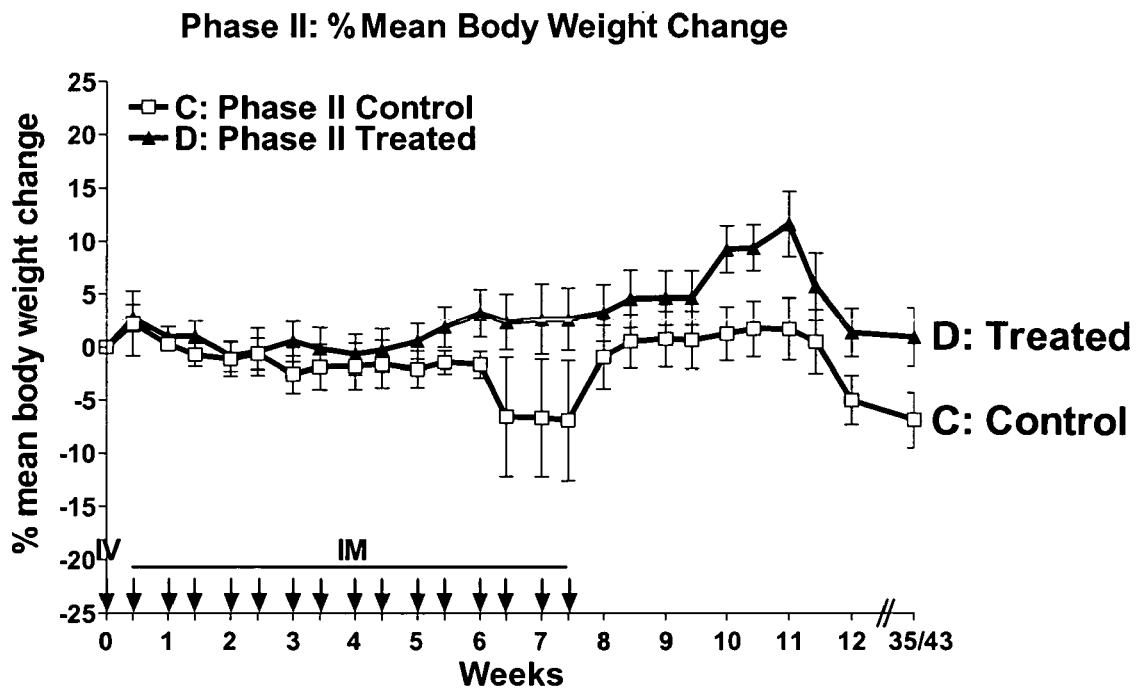
Figure 3A:
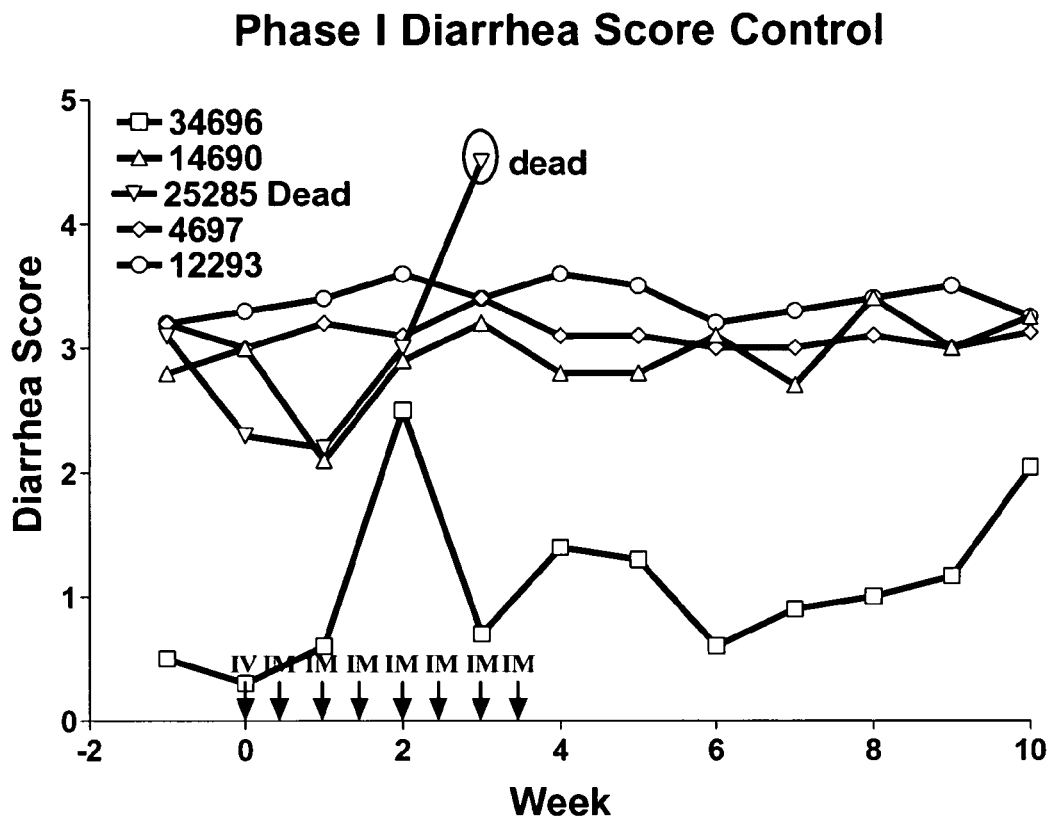
FIGS. 3A-3D and 4A-4D are graphs showing the effect of CPI-1697 on diarrhea scores of IBD-afflicted CTT.
Figure 3B:
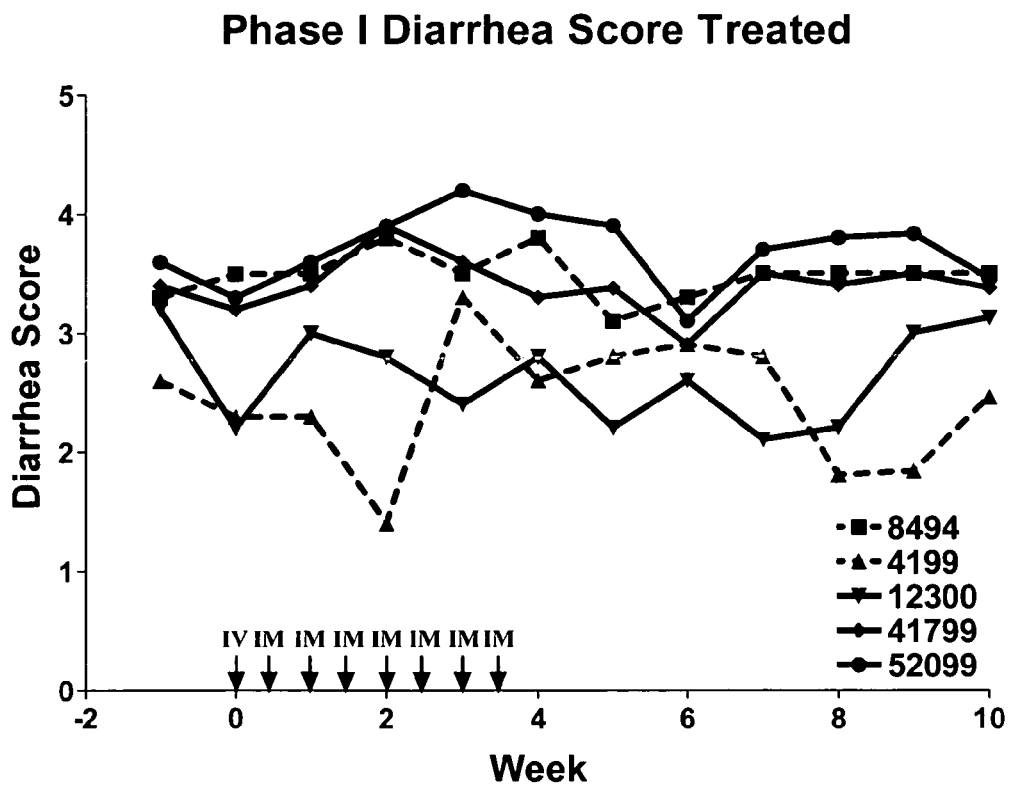
Figure 3C:
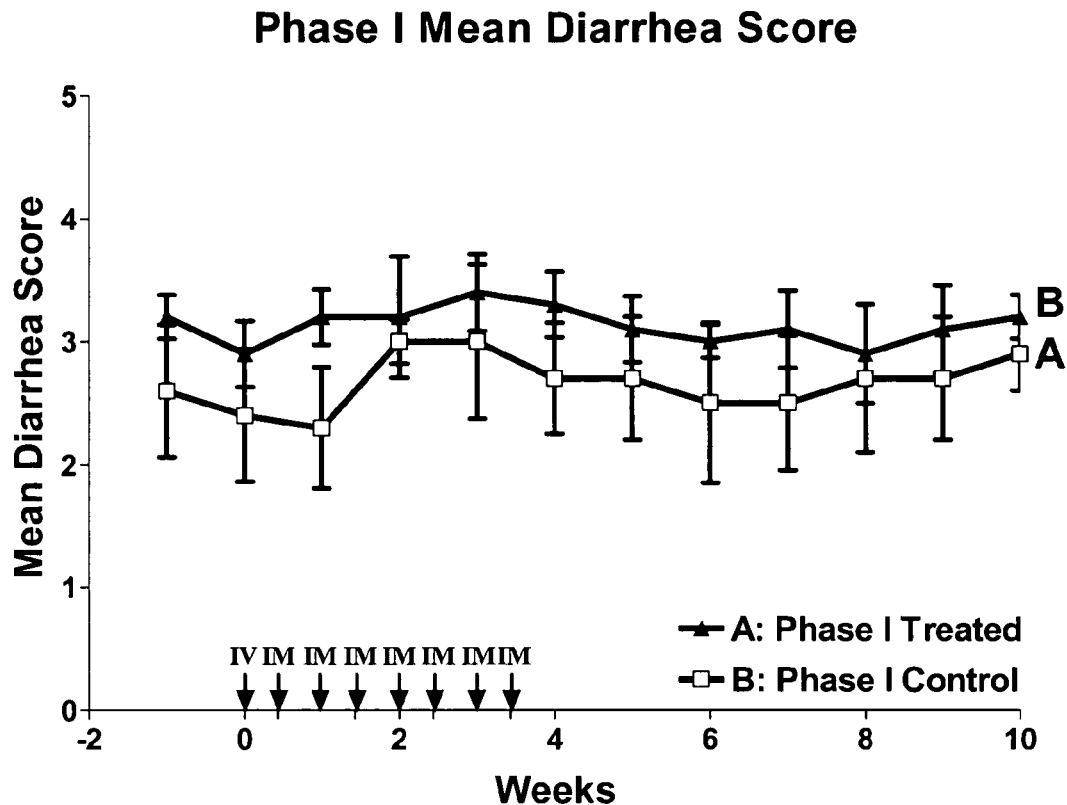
Figure 3D:
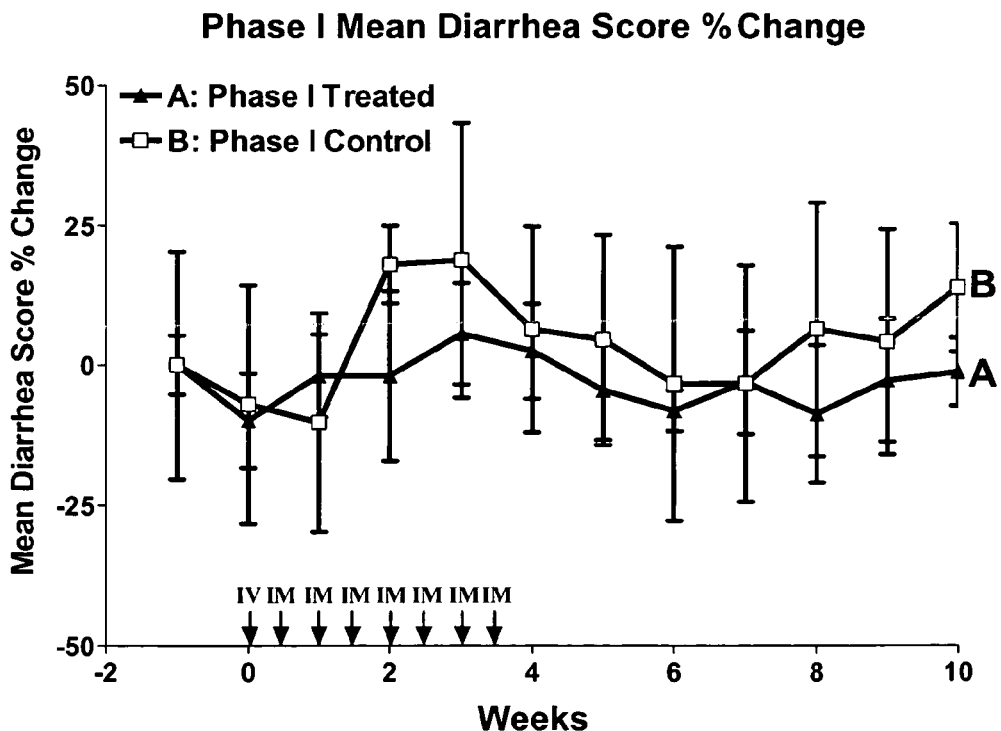
Figure 4A:
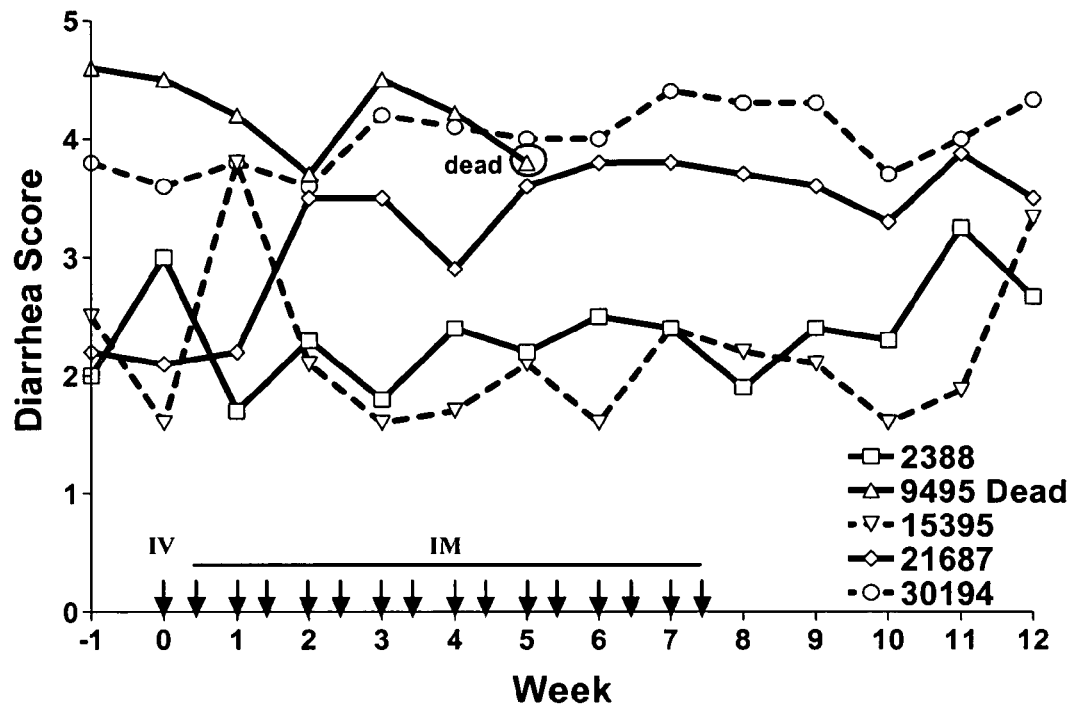
Figure 4B:
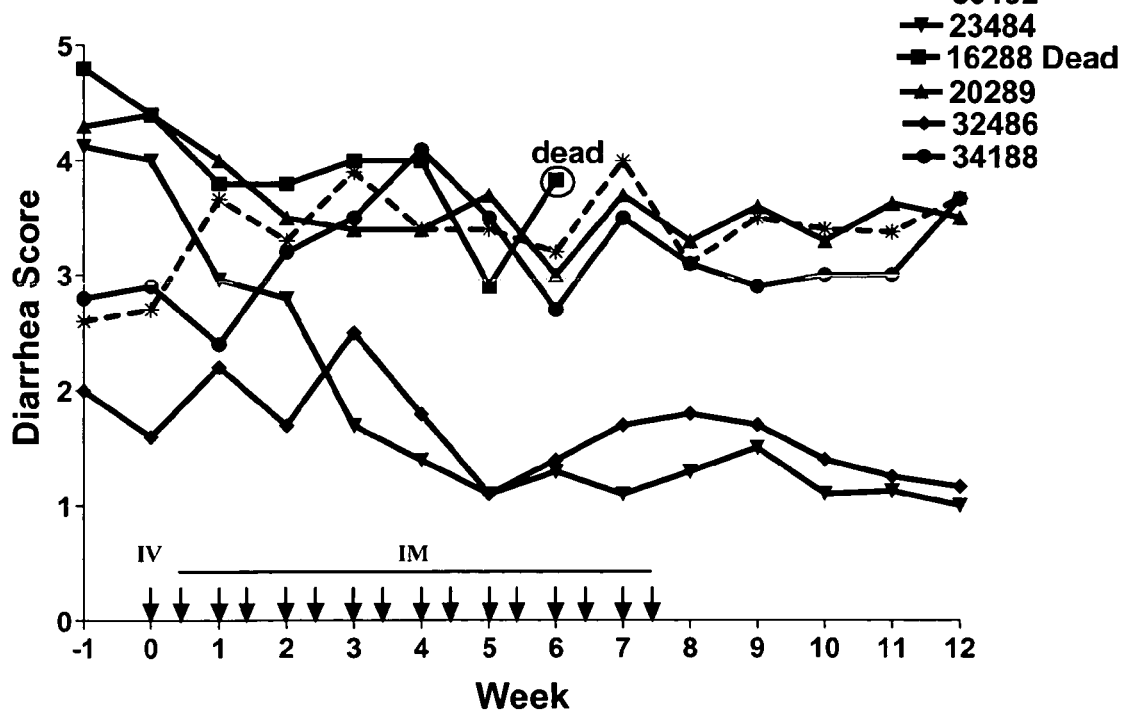
Figure 4C:
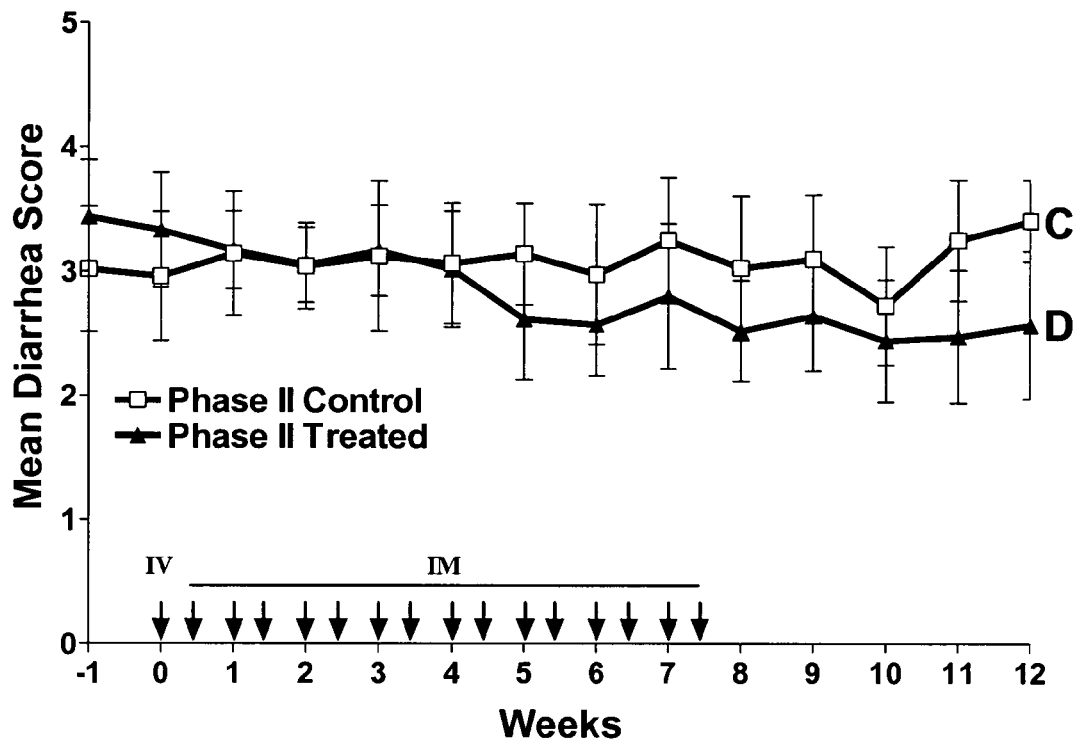
Figure 4D:
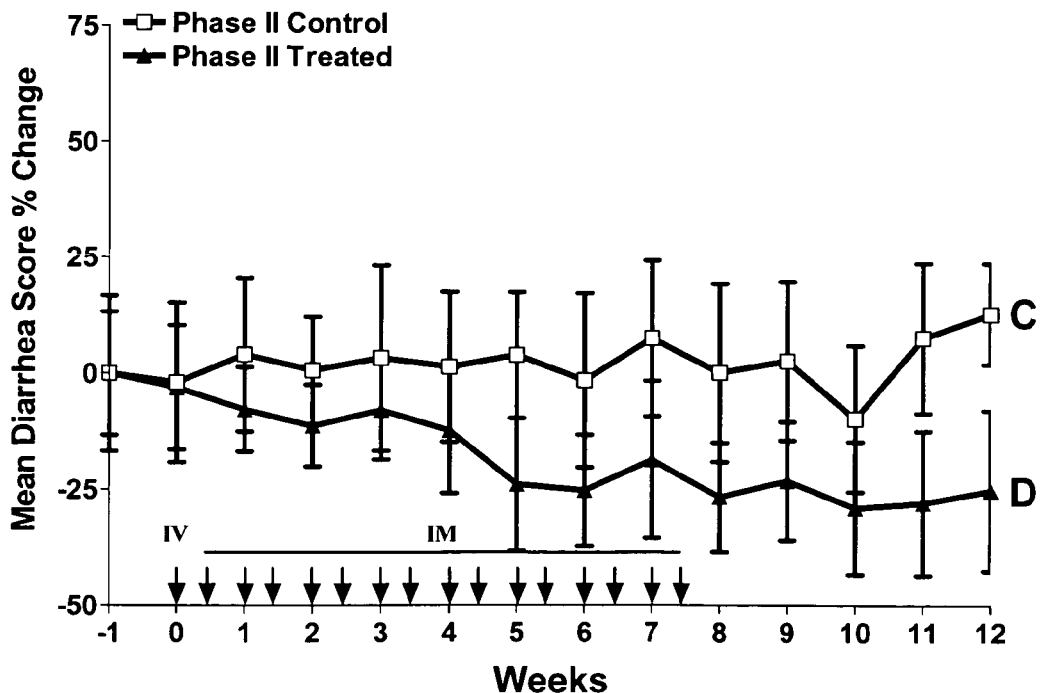
Figure 5A:
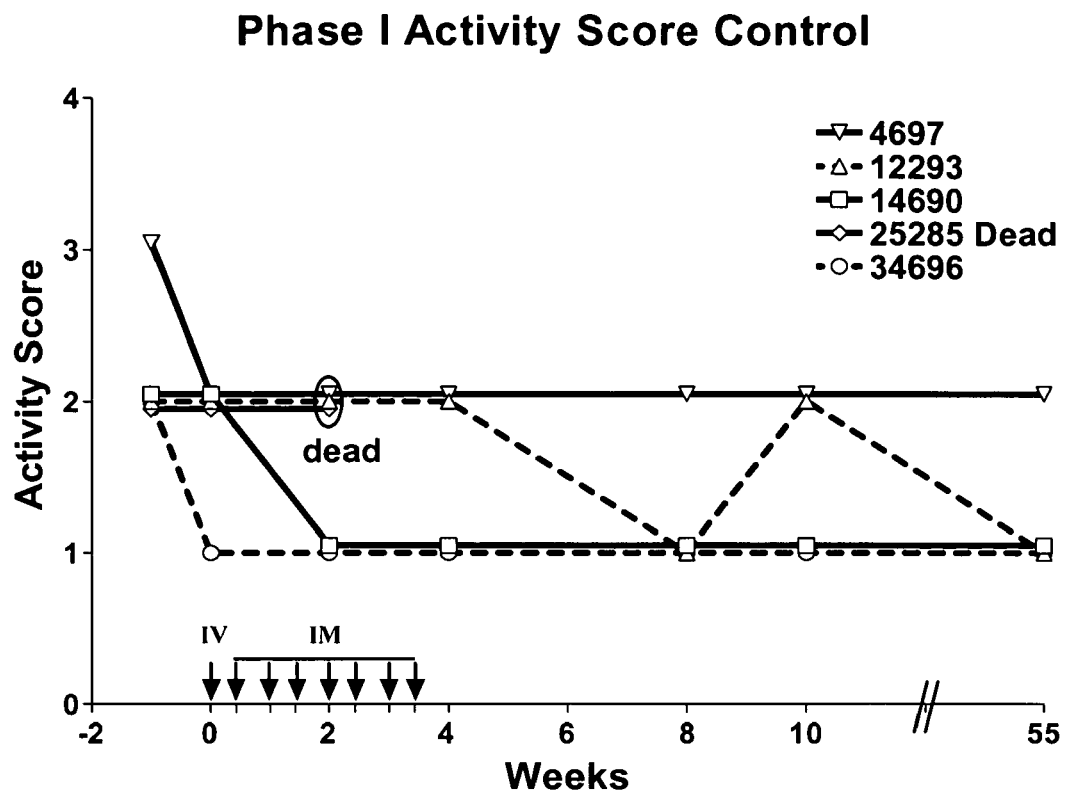
FIGS. 5A-5D and 6A-6D are graphs showing the effect of CPI-1697 on activity scores of IBD-afflicted CTT.
Figure 5B:
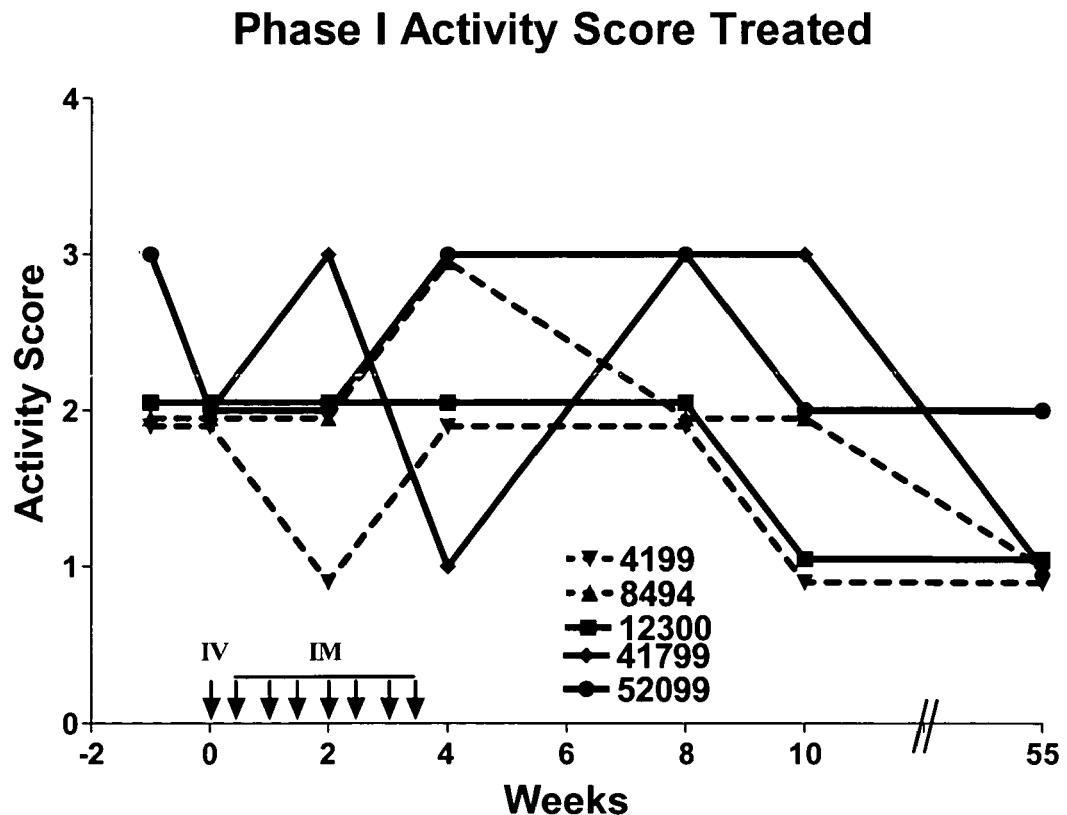
Figure 5C:
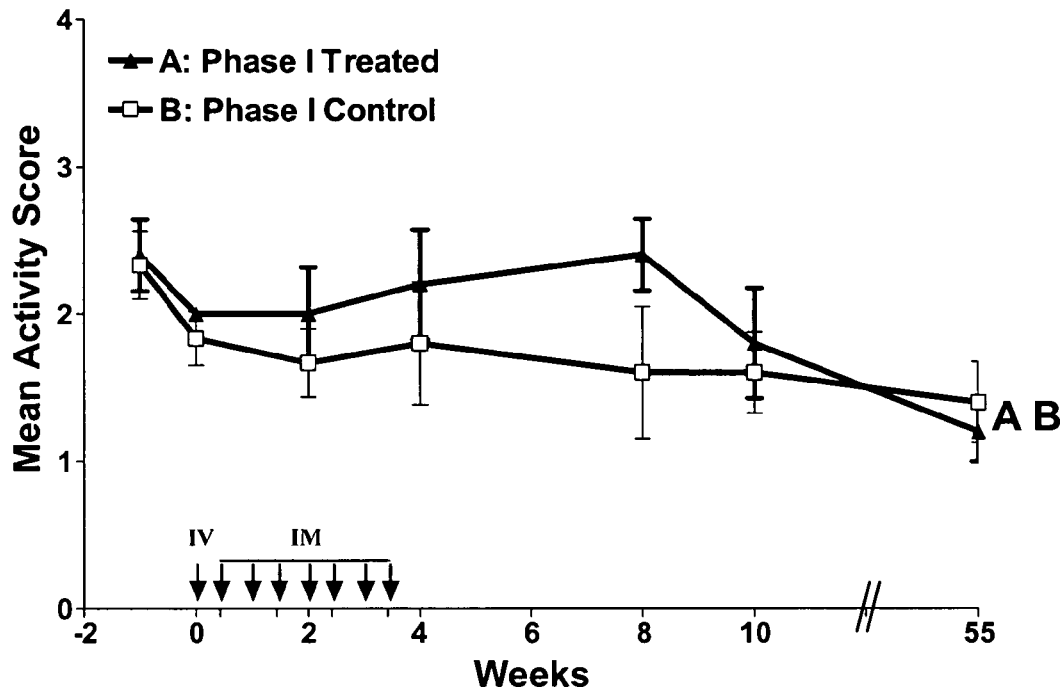
Figure 5D:
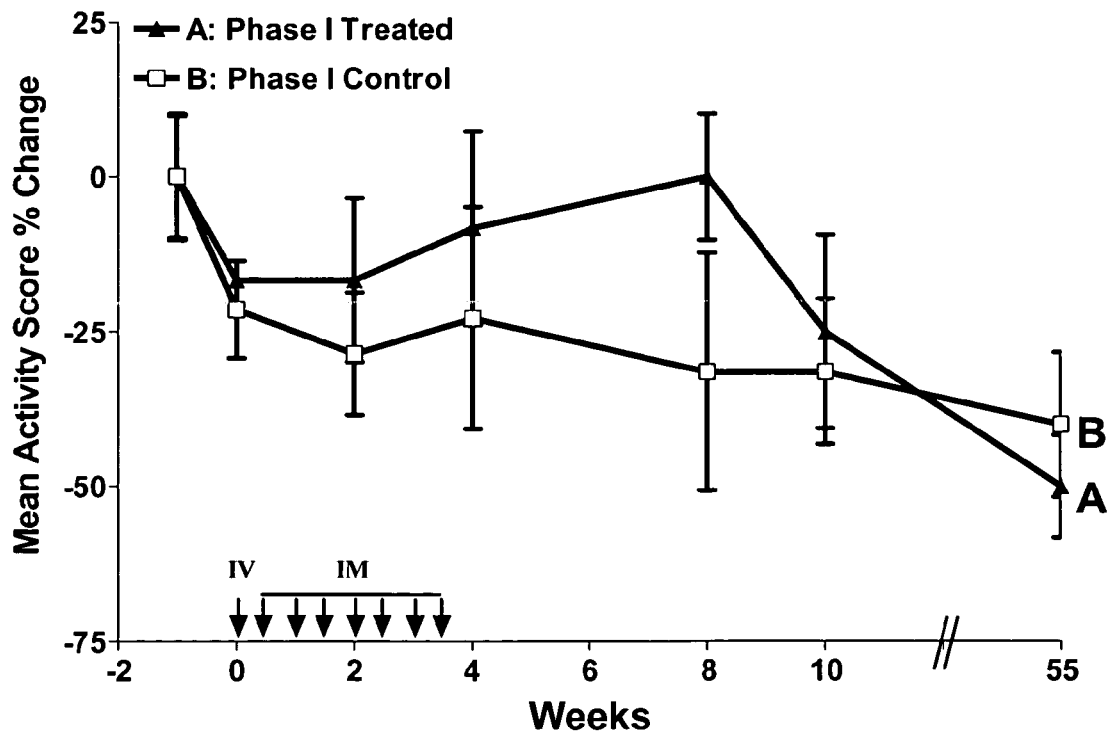
Figure 6A:
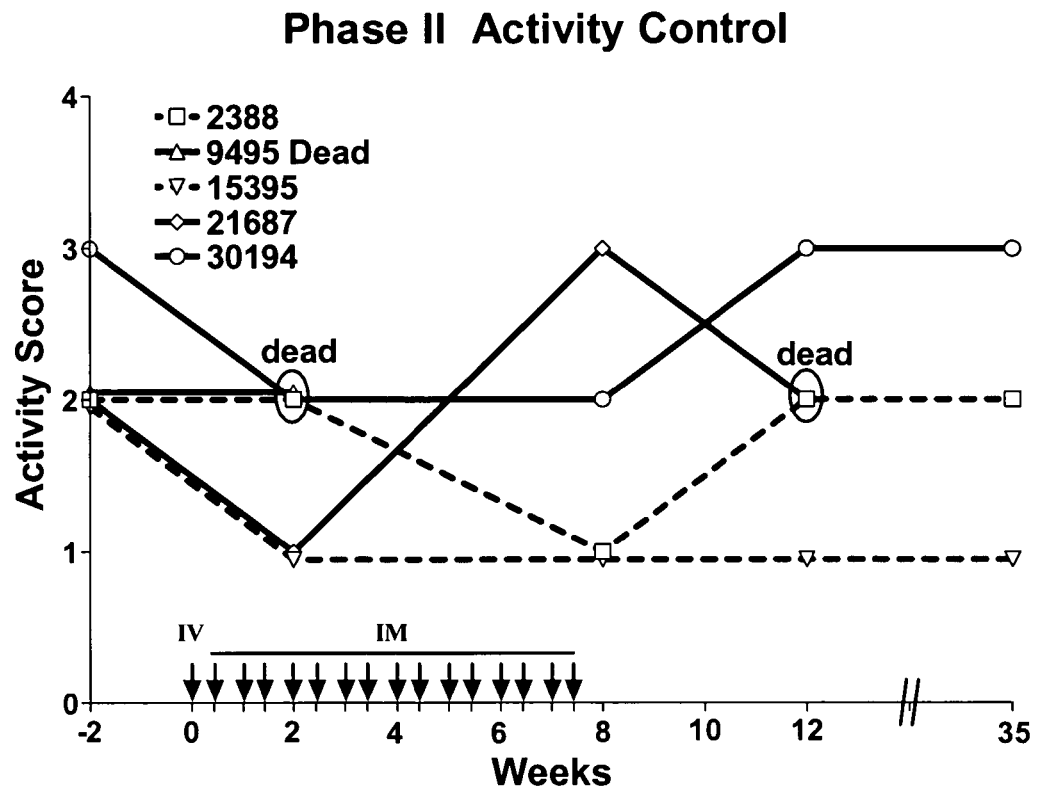
Figure 6B:
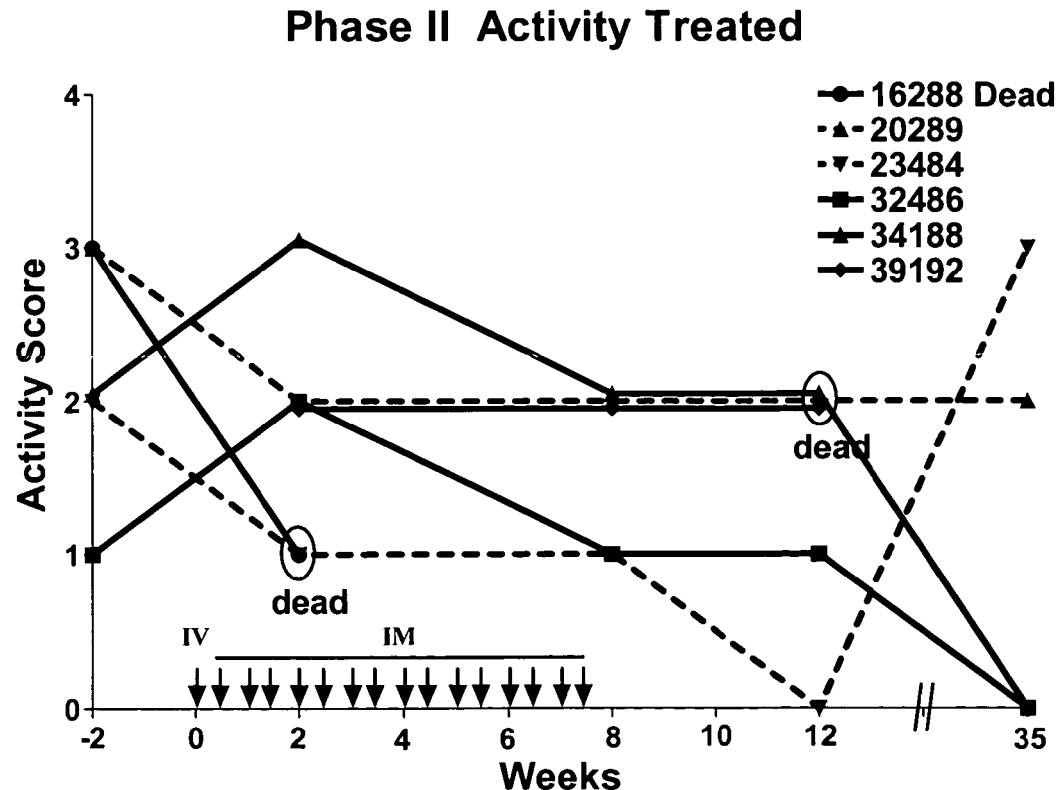
Figure 6C:
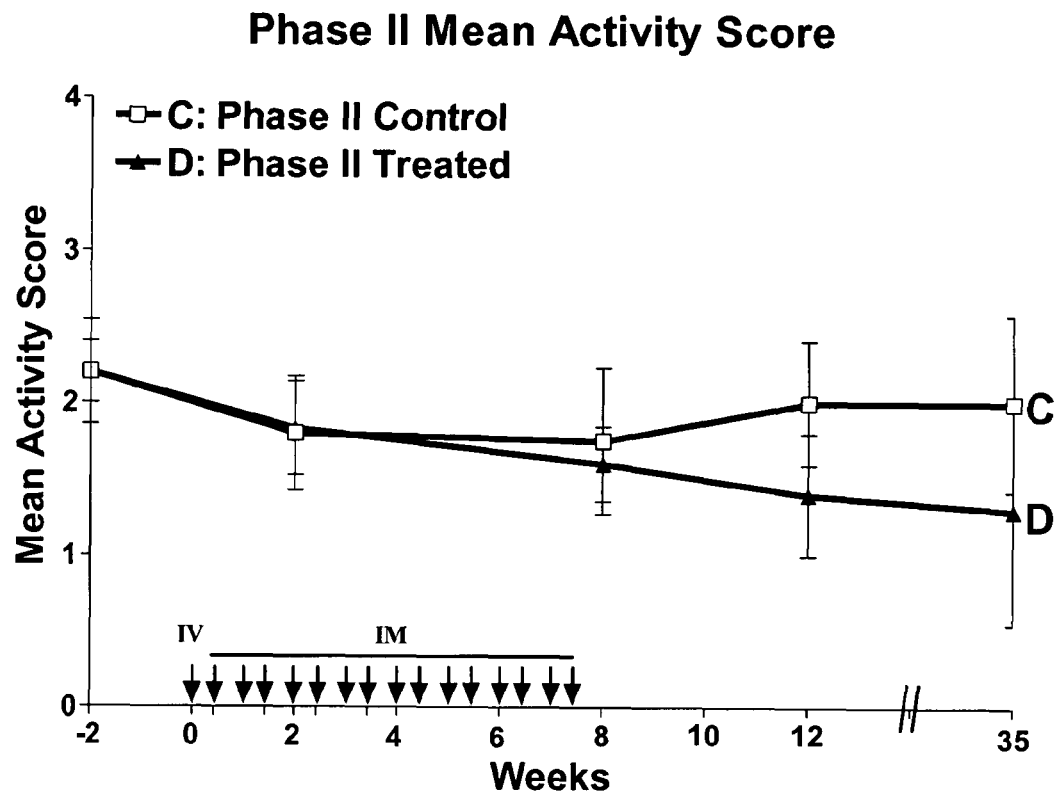
Figure 6D:
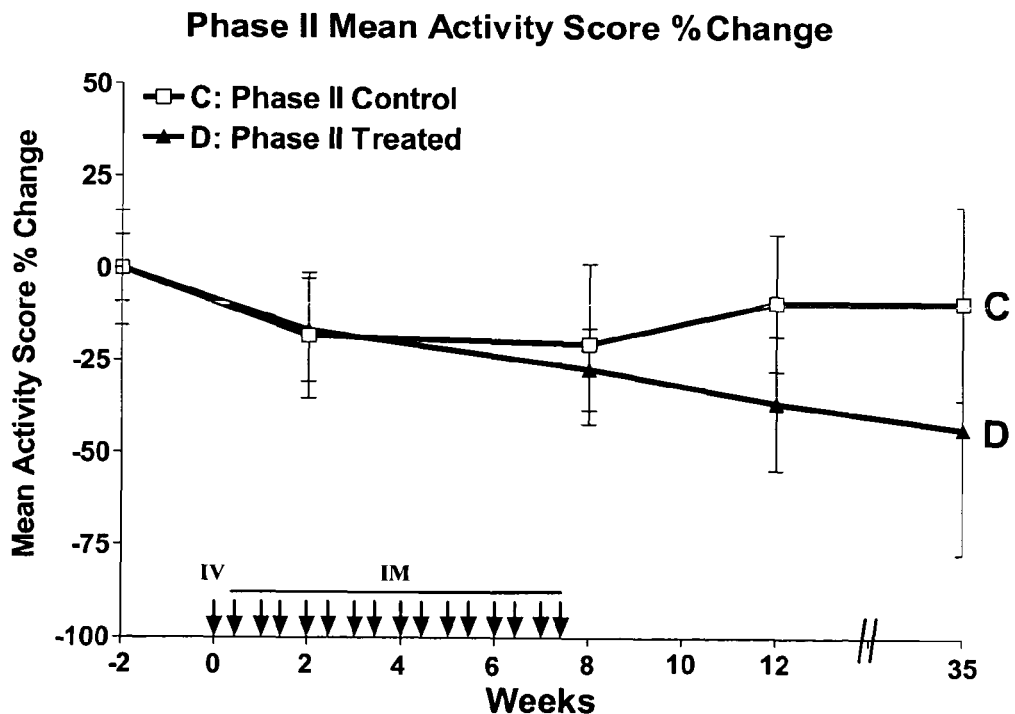
Figure 7A:
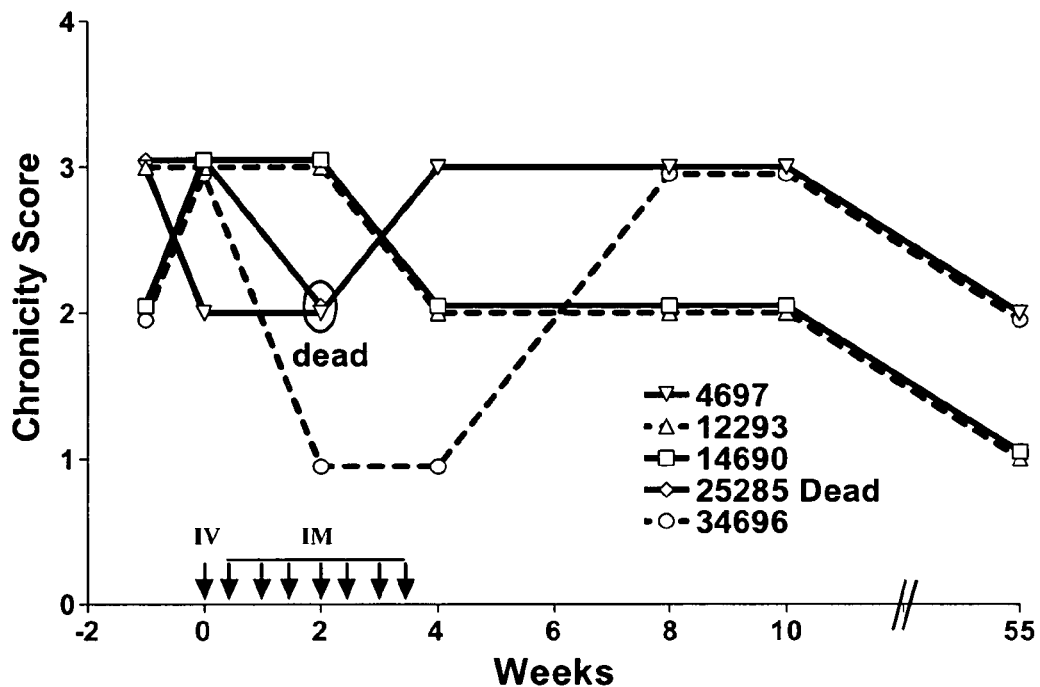
FIGS. 7A-7D and 8A-8D are graphs showing the effect of CPI-1697 on chronicity scores of IBD-afflicted CTT.
Figure 7B:
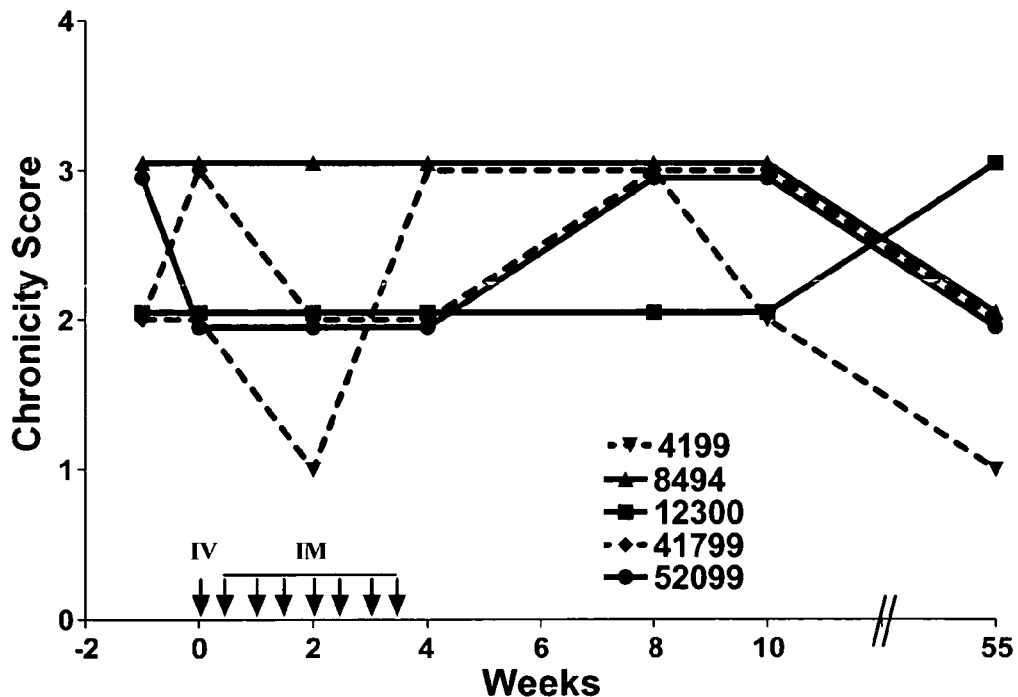
Figure 7C:
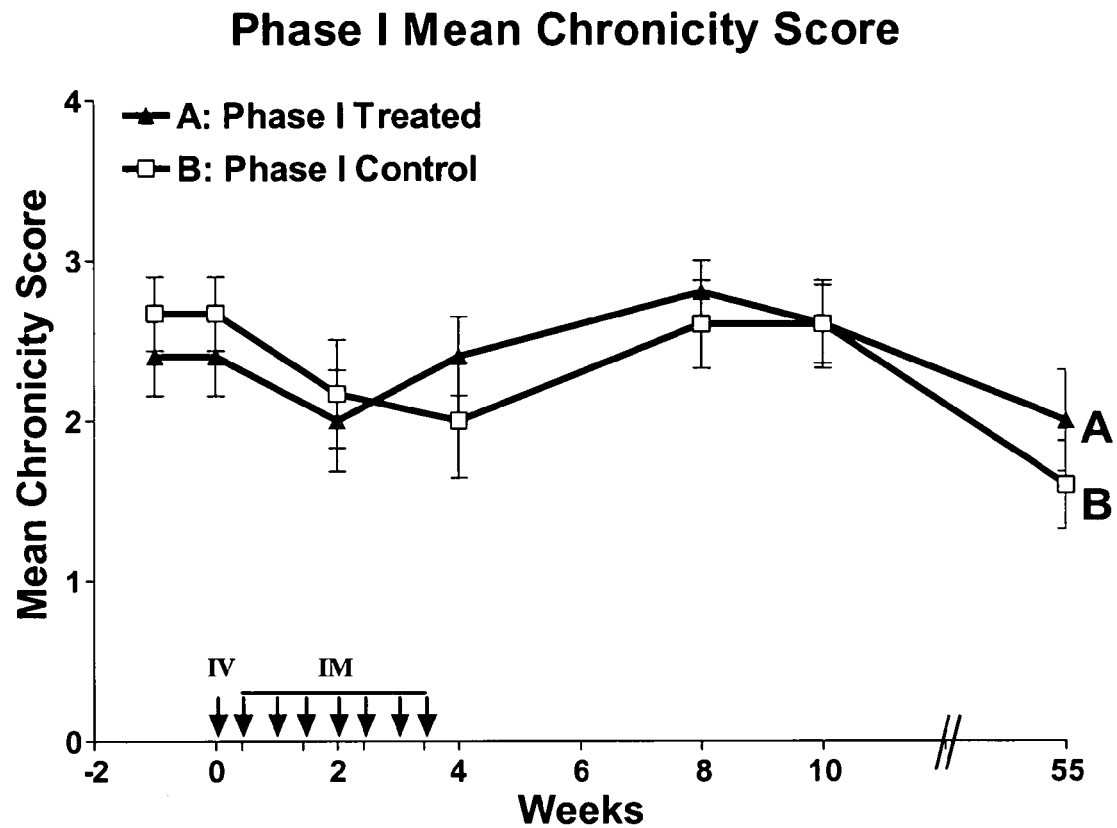
Figure 7D:
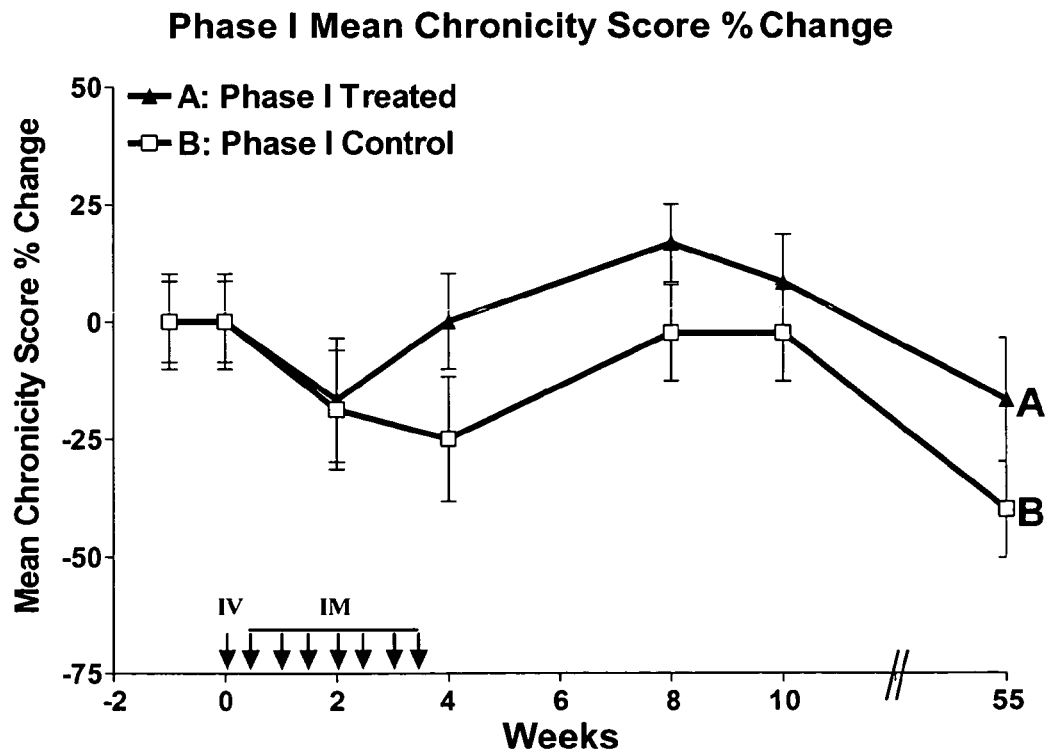
Figure 8A:
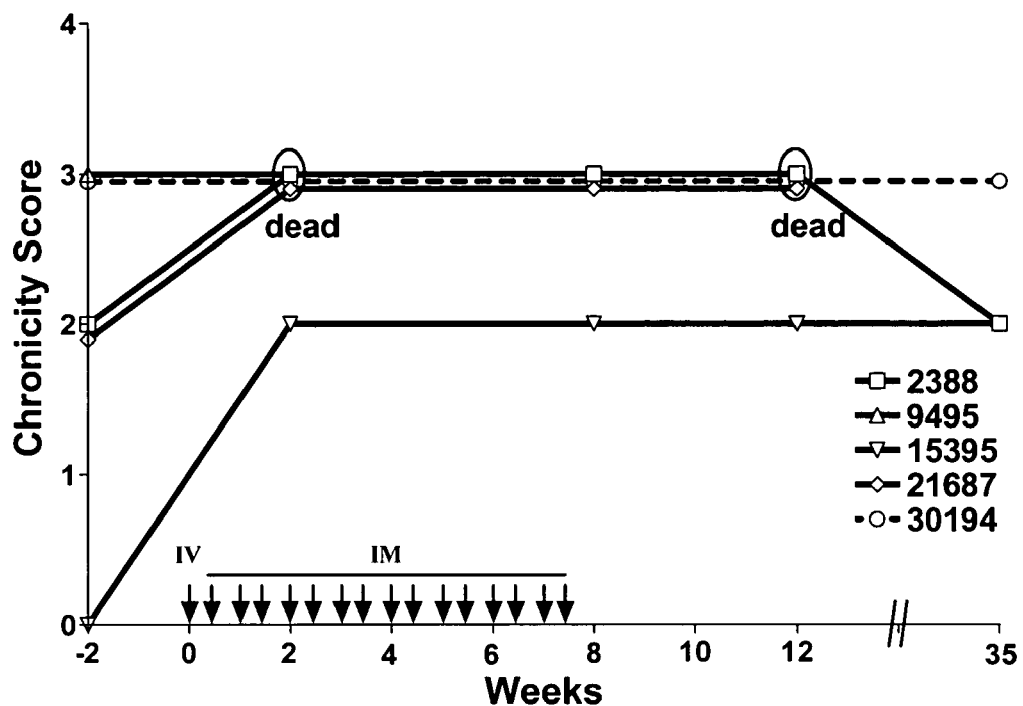
Figure 8B:
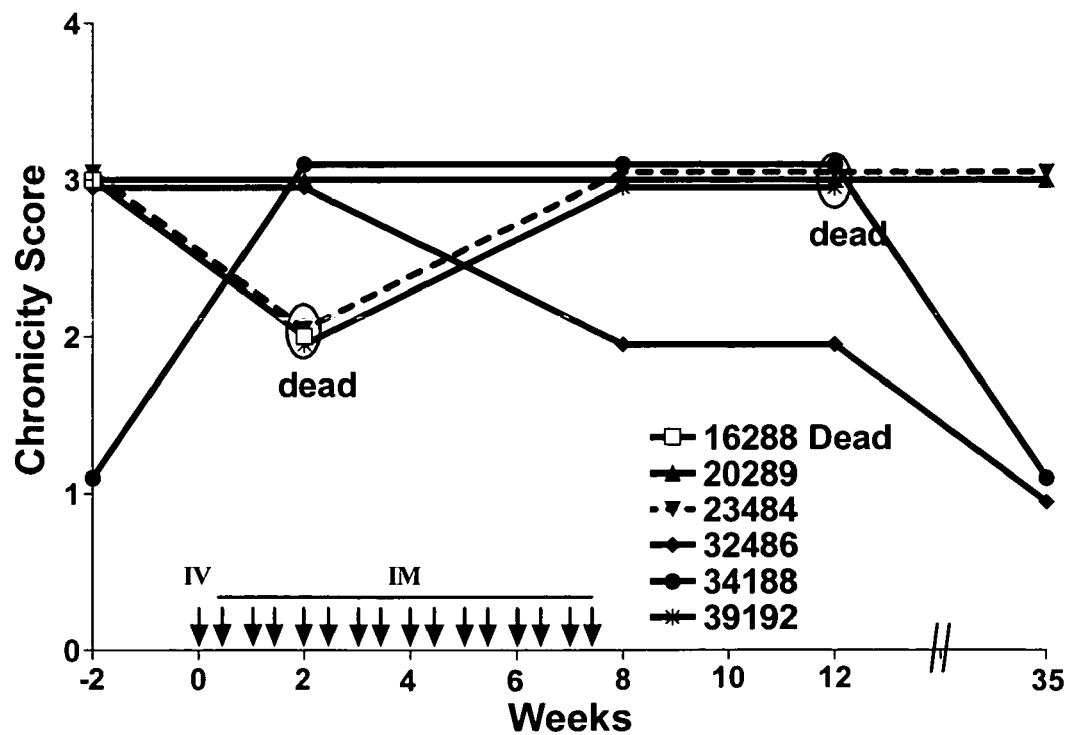
Figure 8C:
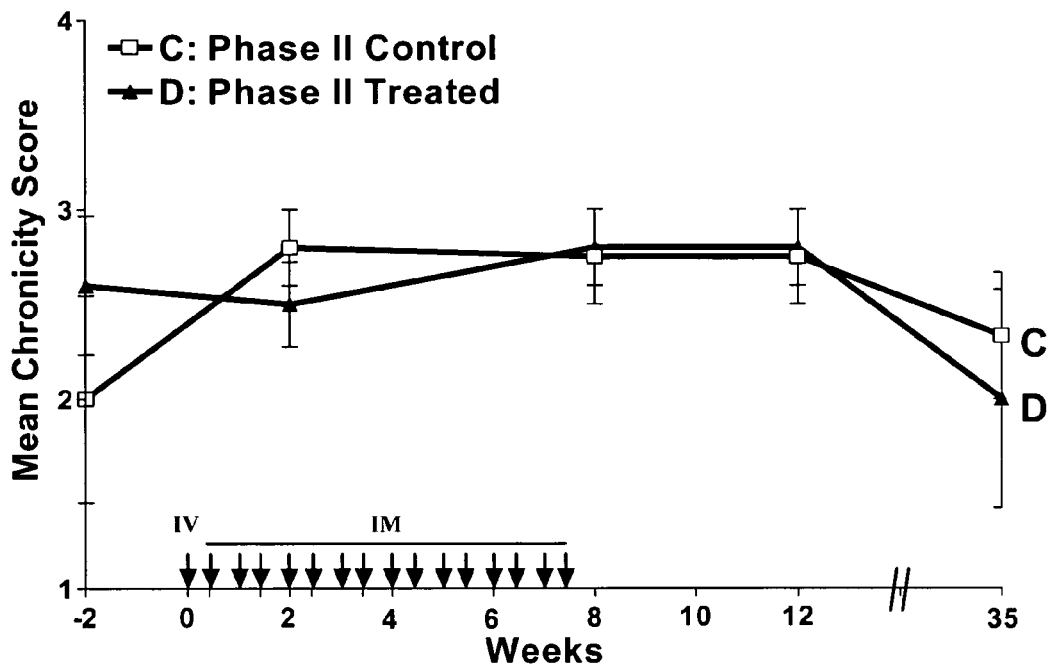
Figure 8D:
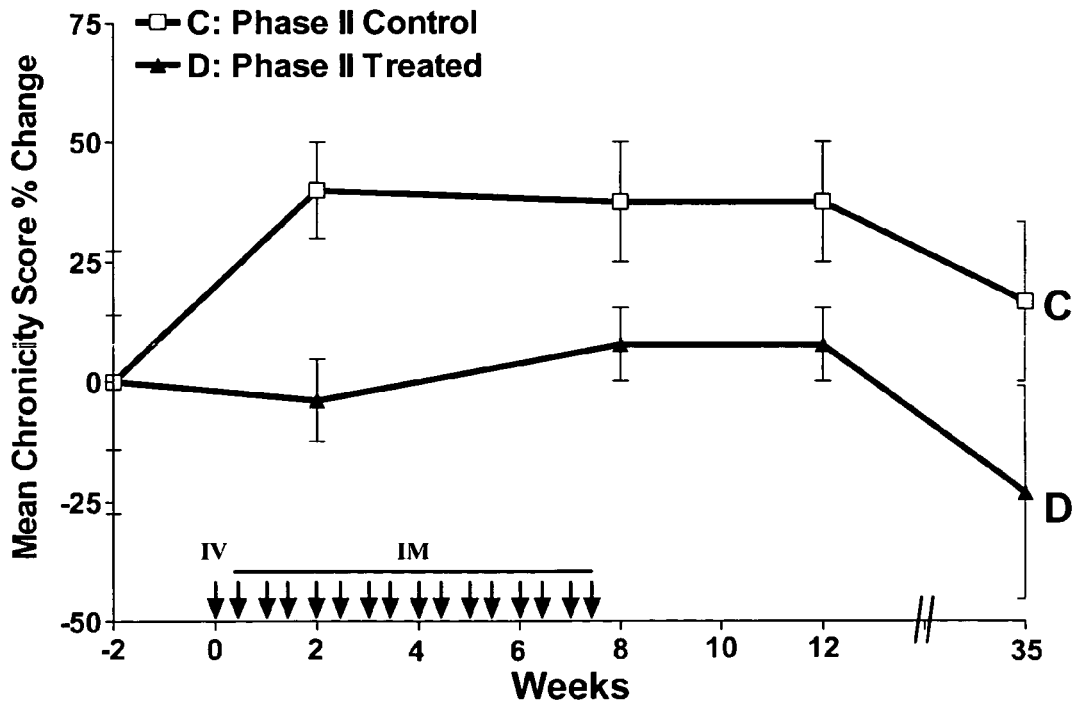
Figure 9A:
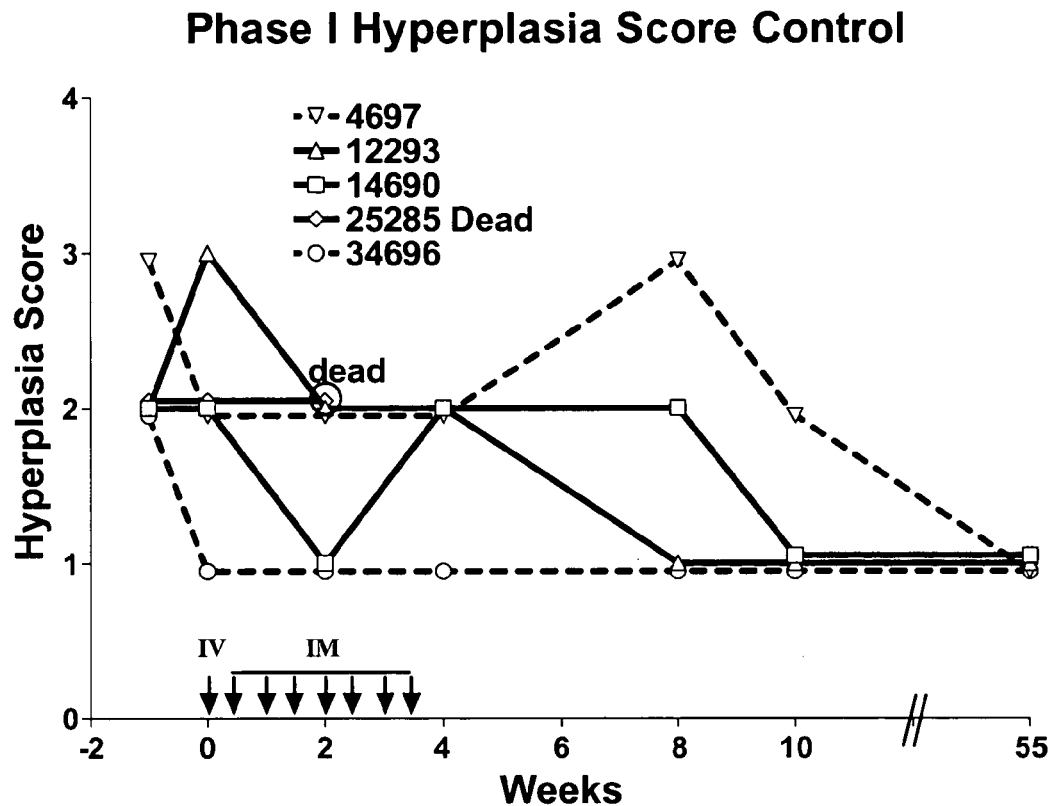
FIGS. 9A-9D and 10A-10D are graphs showing the effect of CPI-1697 on hyperplasia scores of IBD-afflicted CTT.
Figure 9B:
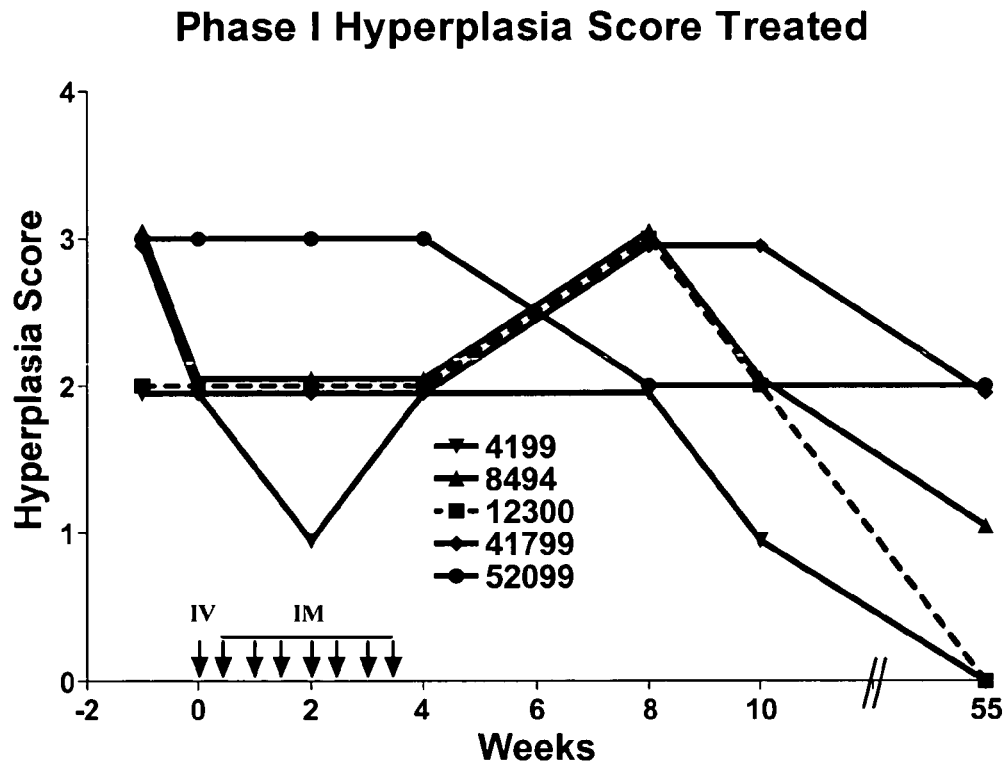
Figure 9C:
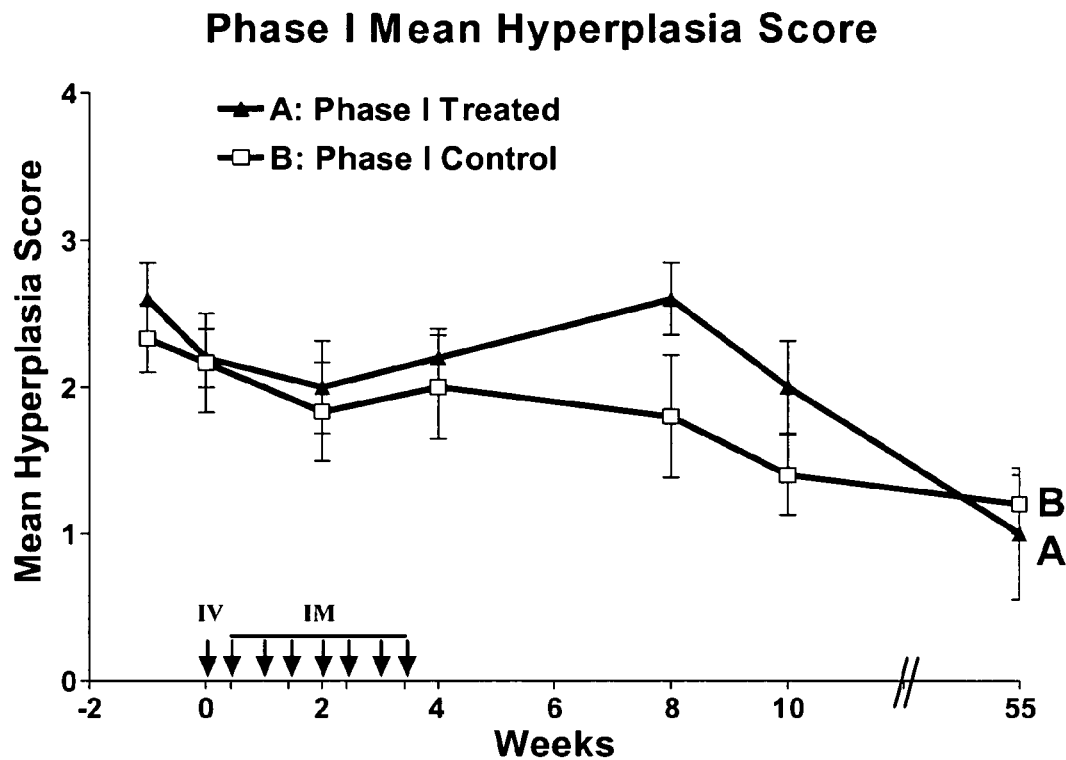
Figure 9D:
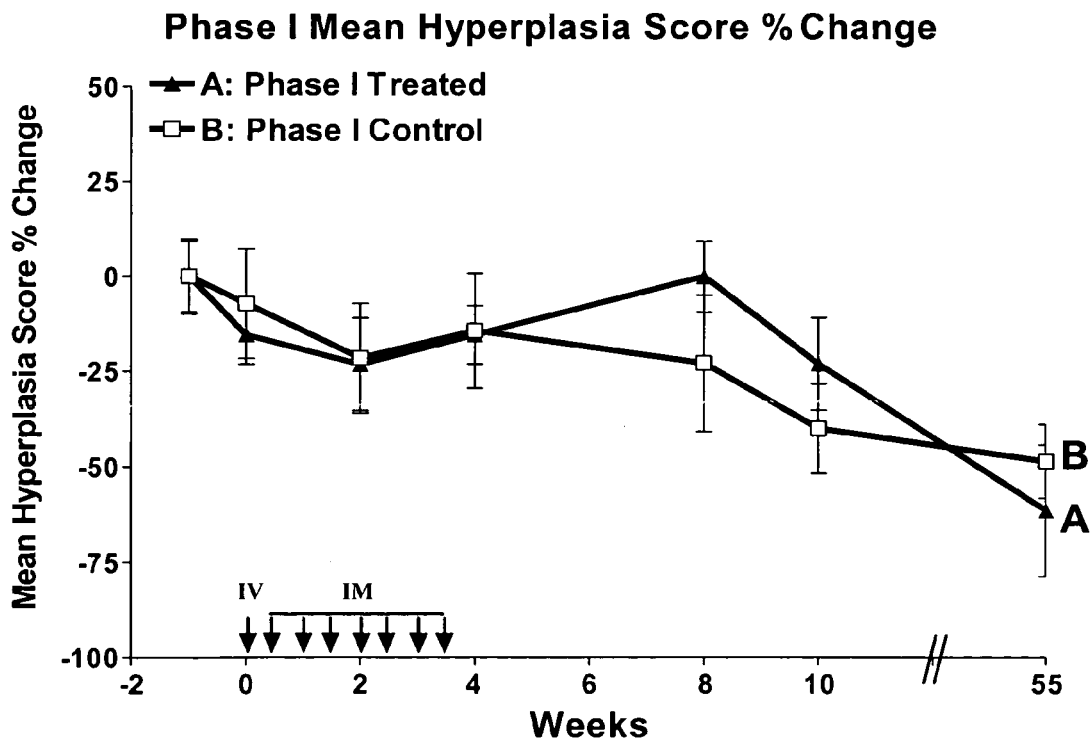
Figure 10A:
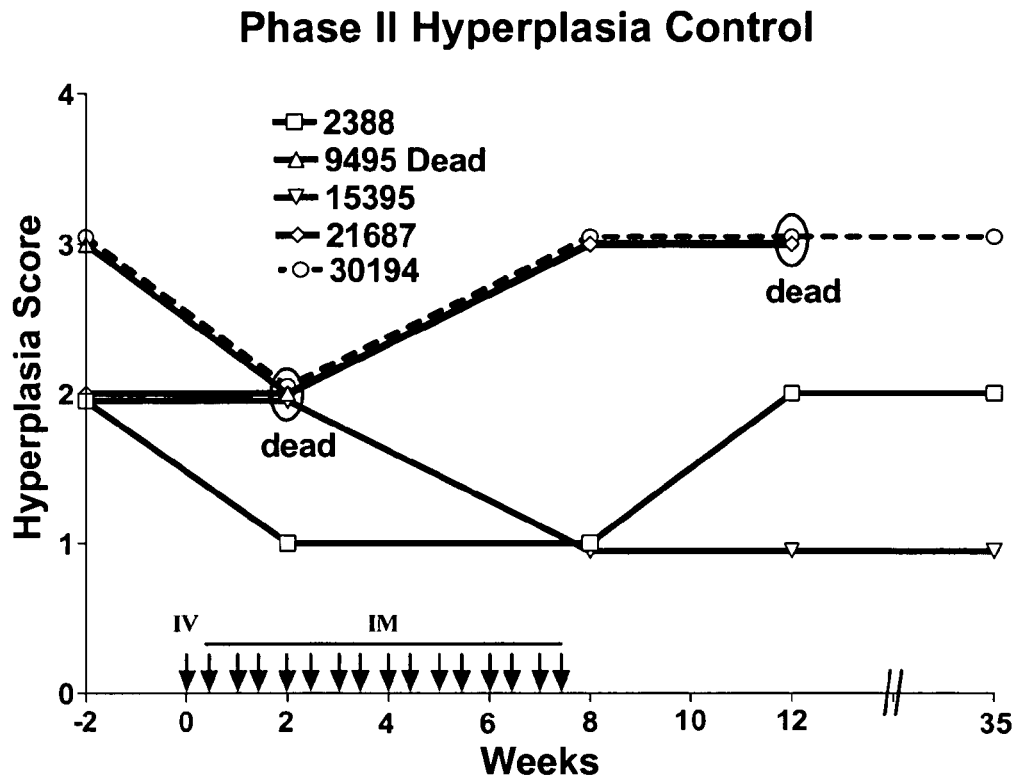
Figure 10B:
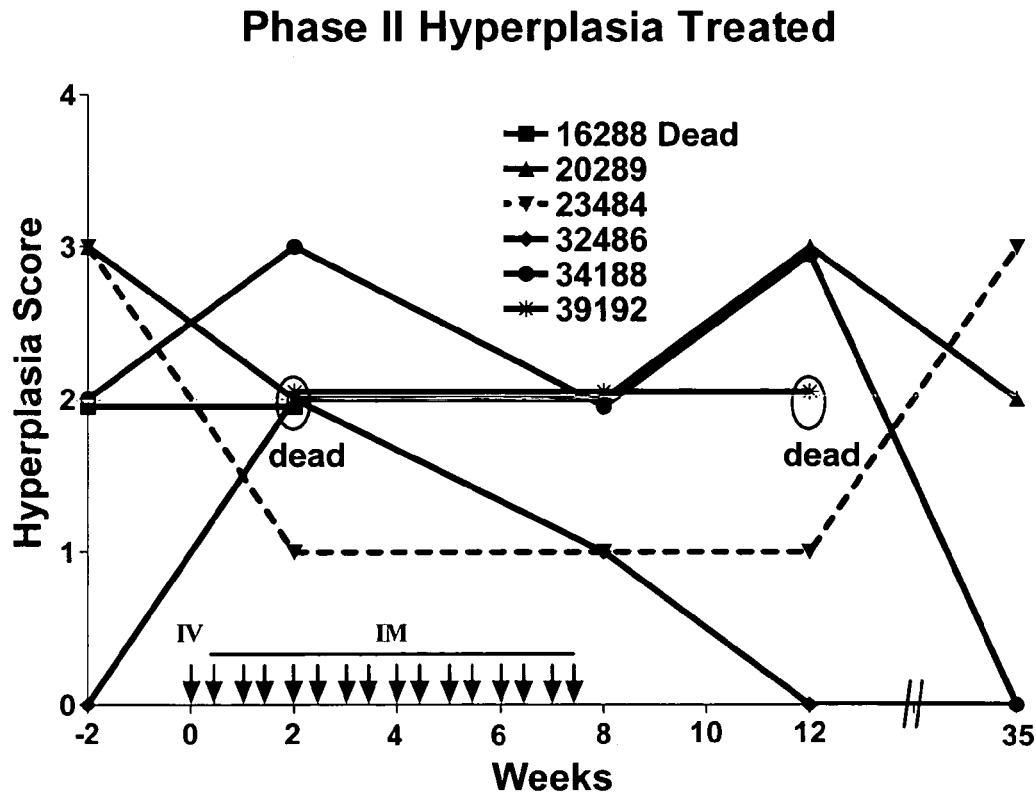
Figure 10C:
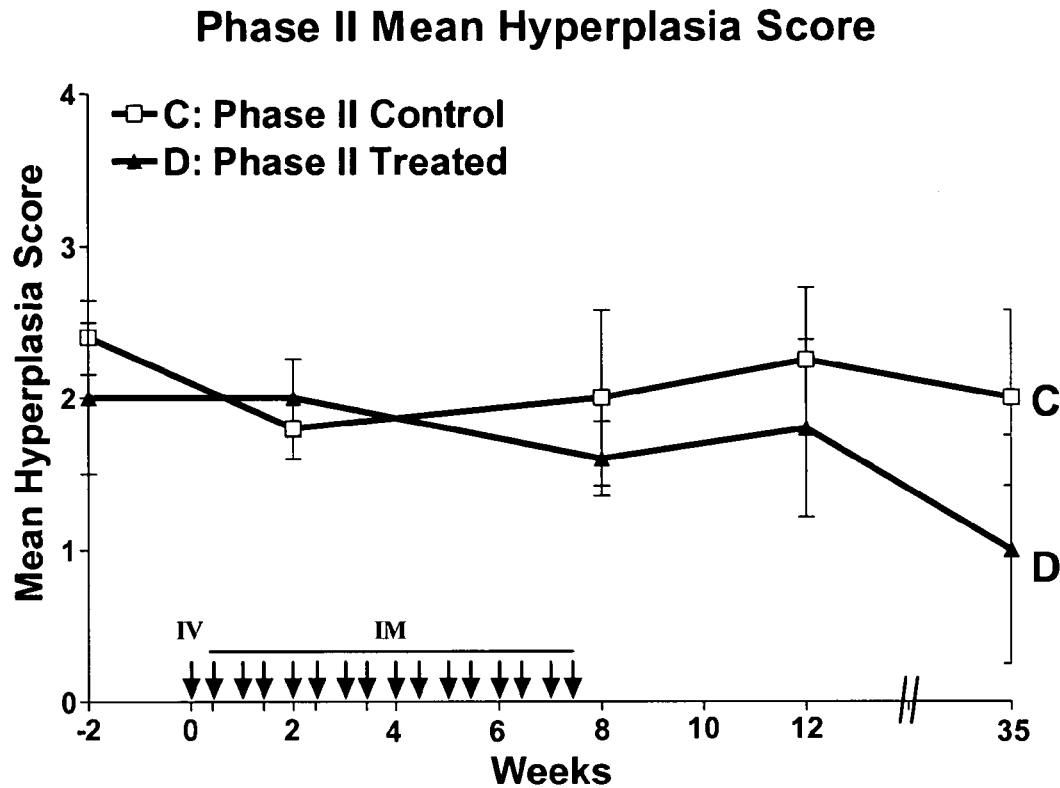
Figure 10D:
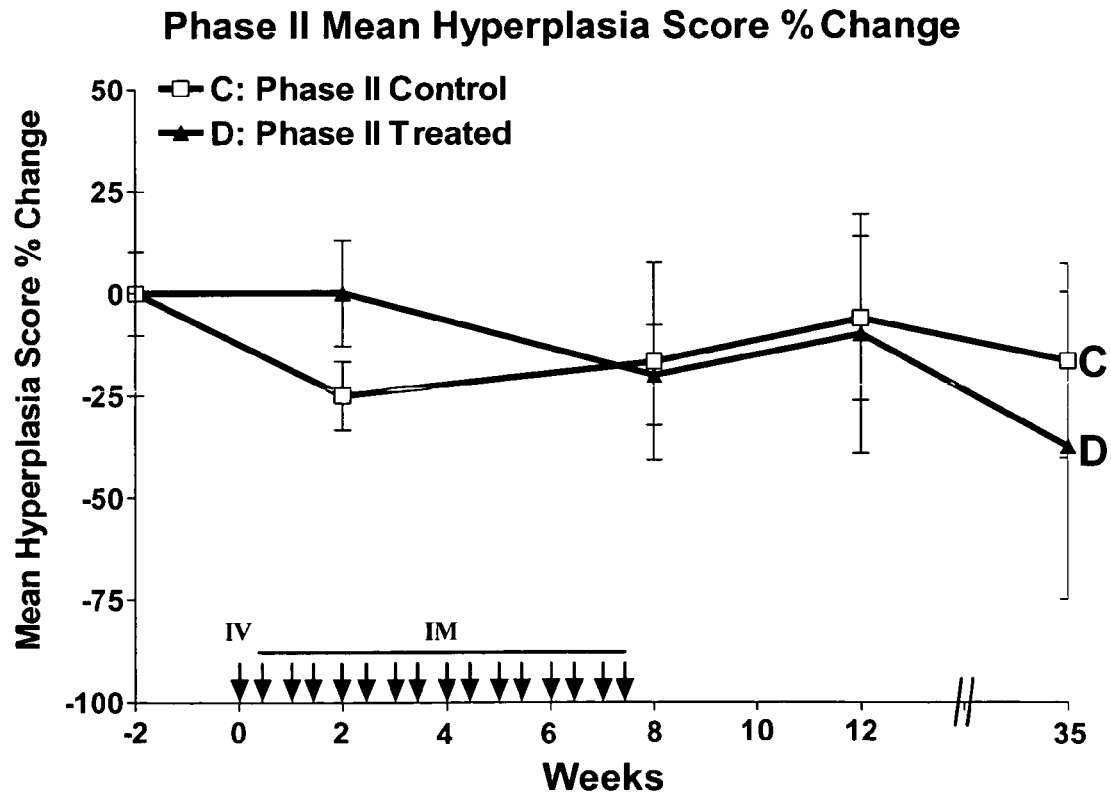

The present invention is directed generally to compositions and their use in therapeutic methods for the treatment of Inflammatory Bowel Disease (IBD), particularly Celiac disease, Crohn's disease, and ulcerative colitis. As described further below, illustrative compositions of the present invention include type 1 interferon antagonists, particularly anti-IFNAR antibodies, anti-type 1 interferon antibodies and/or antigen binding fragments thereof as well as polypeptides and small molecules that function as type 1 interferon antagonists. Without wishing to be limited to any particular theory of operation, exemplary inventive antagonists may interfere and/or compete with ligand binding and/or with interferon-mediated signal transduction. Preferably, type 1 interferon antagonists of the present invention have a long in vivo half-life in circulation and, as a consequence thereof, are effective in achieving a prolonged therapeutic response. Methods for extending in vivo antibody half-lives include, for example, construction of fusion proteins such as immunoglobulin Fc fusions or conjugation to polyethylene glycol (PEGylation).

The present invention further provides therapeutic methods of use which methods employ one or more type 1 interferon antagonist, as indicated above, in the treatment of IBD. Exemplary methods provide long-term response to the type 1 interferon antagonist. Additionally, provided herein are therapeutic methods of use wherein delivery of one or more type 1 interferon antagonist is employed in a tolerizing regimen, that prevents and/or minimizes an immune response to the therapeutic protein, which tolerizing regimen is followed by a therapeutic regimen.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Antibody Type 1 Interferon Antagonists

As noted above, the present invention is directed generally to compositions comprising antagonists of type 1 interferons as well as therapeutic methods of use that employ such compositions for the treatment of Inflammatory Bowel Disease (IBD), particularly Celiac disease, Crohn's disease, and ulcerative colitis. Within certain embodiments of the present invention, type 1 interferon antagonists include anti-IFNAR antibodies and/or fragments thereof that bind to a type 1 interferon receptor and thereby block the binding of its ligand (i.e. interferon alpha, interferon beta or interferon omega). Alternatively or additionally, type 1 interferon antagonists may be anti-type 1 interferon antibodies and/or fragments thereof that bind to a type 1 interferon (i.e. interferon alpha, interferon beta or interferon omega) and thereby block its binding to its receptor (i.e. IFNAR). Antibody-mediated inhibition of ligand binding may occur through competitive, non-competitive or uncompetitive inhibition. Alternatively, antibody-based antagonists may act by preventing intracellular signaling through the type 1 interferon receptor.

Thus, included within the scope of the present invention are chimeric, primatized, veneered, humanized, deimmunized and human anti-IFNAR and anti-type 1 interferon antibodies and/or antigen-binding fragments thereof. Thus, and as disclosed further herein, inventive antibodies encompass portions, variants and/or derivatives of any of the foregoing antibodies.

An antibody, or antigen-binding fragment thereof, is said to "specifically bind," "immunogically bind," and/or is "immunologically reactive" to a type 1 interferon receptor if it reacts at a detectable level (within, for example, an ELISA assay) to IFNAR or to a type 1 interferon, but not to a type 2 interferon receptor, interferon-γ or to any other protein.

"Immunological binding," as used herein, generally refers to the non-covalent interactions of the type that occurs between an antibody, or fragment thereof, and the type 1 interferon or receptor for which the antibody is specific. The strength, or affinity, of immunological binding interactions can be expressed in terms of the dissociation constant ($K_d$) of the interaction, wherein a smaller $K_d$ represents a greater affinity. Immunological binding properties of selected antibodies can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al., Annual Rev. Biochem. 59:439-473 (1990).

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Antibodies may be prepared by any of a variety of techniques known to those of ordinary skill in the art. See, e.g., Harlow and Lane, *Antibodies: A Laboratory Manual*, Cold Spring Harbor Laboratory (1988). In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising type 1 interferon receptor or portion thereof is initially injected into any of a wide variety of mammals (e.g., mice, rats, rabbits, sheep, hamsters, goats or transgenic mice with human antibody repertoires). Alternatively, the immunogen may comprise cells or cell extracts containing receptor, extracellular domains of the receptor (natural or recombinant). A superior immune response may be elicited if type 1 interferon receptor is joined to a carrier protein, such as bovine serum albumin or keyhole limpet hemocyanin (KLH). The immunogen is injected into the animal host, preferably according to a predetermined schedule incorporating one or more booster immunizations, and the animals are bled periodically. Immunization may be carried out with one or more adjuvants such as complete and incomplete Freund's adjuvant. Polyclonal antibodies specific for the type 1 interferon receptor may then be purified from such antisera by, for example, affinity chromatography using type 1 interferon receptor immunogenic regions coupled to a suitable solid support.

Monoclonal antibodies specific for a type 1 interferon receptor may be prepared, for example, using the technique of Kohler and Milstein, Nature 256(5517):495-7 (1975), and improvements thereto. Briefly, these methods involve the preparation of immortal cell lines capable of producing antibodies having the desired specificity (i.e., reactivity with the ganglioside of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against a type 1 interferon receptor. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Anti-type 1 interferon receptor may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "$F_{ab}$" fragments) each comprise a covalent heterodimer that includes an intact antigen-binding site. The enzyme pepsin is able to cleave IgG molecules to provide several fragments, including the "$F_{ab'2}$" fragment which comprises both antigen-binding sites. An "$F_v$" fragment can be produced by preferential proteolytic cleavage of an IgM, and on rare occasions IgG or IgA immunoglobulin molecule. $F_v$, $F_{ab}$ and $F_{ab'2}$ fragments are, however, more commonly derived using recombinant techniques known in the art. The $F_v$ fragment includes a non-covalent $V_H::V_L$ heterodimer including an antigen-binding site which retains much of the antigen recognition and binding capabilities of the native antibody molecule. Inbar et al. Proc. Nat. Acad. Sci. USA 69:2659-2662 (1972); Hochman et al. Biochem 15:2706-2710 (1976); and Ehrlich et al. Biochem 19:4091-4096 (1980).

A single chain $F_v$ ("$sF_v$") antibody is a covalently linked $V_H::V_L$ heterodimer which is expressed from a gene fusion including $V_H$- and $V_L$-encoding genes linked by a peptide-encoding linker. Huston et al., Proc. Nat. Acad. Sci. USA 85(16):5879-5883 (1988). A number of methods have been described to discern chemical structures for converting the naturally aggregated—but chemically separated—light and heavy anti-anti-type 1 interferon receptor antibody chains from an antibody V region into an $sF_v$ molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A type 1 interferon antagonist comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences that frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino acid residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including antibodies having their associated non-human V-regions fused to human constant domains (Winter and Milstein Nature 349:293-299 (1991); Lobuglio et al. Proc. Nat. Acad. Sci. USA 86:4220-4224 (1989); Shaw et al. J. Immunol. 138:4534-4538 (1987); and Brown et al. Cancer Res. 47:3577-3583 (1987)), non-human CDRs grafted into a human supporting FR prior to fusion with an appropriate human antibody constant domain (Riechmann et al. Nature 332:323-327 (1988); Verhoeyen et al. Science 239:1534-1536 (1988); and Jones et al. Nature 321:522-525 (1986)), and rodent CDRs supported by recombinantly veneered rodent FRs (European Patent Publication No. 519,596, published Dec. 23, 1992). These "humanized" molecules are designed to minimize unwanted immunological response toward non-human antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR folding structure. Veneering techniques are based on the understanding that the ligand binding characteristics of an antigen-binding site are determined primarily by the structure and relative disposition of the heavy and light chain CDR sets within the antigen-binding surface. Davies et al. Ann. Rev. Biochem. 59:439-473 (1990). Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

The present invention also contemplates that it may be desirable to reduce the in vivo immunogenicity or any of the antibodies prepared as outlined above or by methods otherwise available in the art. One exemplary approach for achieving antibodies having reduced immunogenicity is the DeImmunisation™ methodology provided by Biovation (Aberdeen, U.K.). By this methodology, human helper T-cell epitopes that comprise MHC class II binding sequences are identified and removed from therapeutic antibodies in order to minimize activation and differentiation of helper T-cells when the antibody is administered in vivo.

A preferred antibody of the invention is a humanized antibody referred to herein as CPI-1697. This antibody is composed of a heavy chain referred to as H3 and a light chain referred to as K1. The amino acid sequences of the H3 heavy chain and K1 light chain variable regions are shown in FIGS. 14A (SEQ ID NO:1) and 14B (SEQ ID NO:2). The H3 heavy chain contains the CDR1, CDR2 and CDR3 sequences from the heavy chain of the murine anti-IFNAR-1 antibody 64G12, grafted onto a consensus human immunoglobulin heavy chain framework sequence, whereas the K1 light chain contains the CDR1, CDR2 and CDR3 sequences from the light chain of the murine anti-IFNAR-1 antibody 64G12, grafted onto a consensus human immunoglobulin kappa light chain framework sequence. The CPI-1697 antibody further includes a human IgG4 constant region.

Other antibody-based IFNAR-1 antagonists suitable for use in the invention are described in detail in the co-owned U.S. patent application entitled "Humanized Antibodies to Interferon Alpha Receptor-1 (IFNAR-1)", Ser. No. 60/465,058, filed on Apr. 23, 2003, the entire contents of which are expressly incorporated herein by reference.

Small Molecule and Polypeptide Type 1 Interferon Antagonists

In addition to antibody-based type 1 interferon antagonists, the present invention also contemplates type 1 interferon antagonists, and compositions thereof, comprising one or more small molecules such as, for example, those small molecules that interfere with binding of a type 1 interferon with its receptor (i.e. IFNAR).

In certain embodiments, combinatorial libraries of potential small molecule antagonists may be screened for an ability to bind to a type 1 interferon or to the type 1 interferon receptor. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual IBD therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks. Gallop et al., J. Med. Chem. 37(9): 1233-1251 (1994).

Preparation and screening of combinatorial chemical libraries is well known to those of skill in the art. Such combinatorial chemical libraries include, but are not limited to, peptide libraries (see, e.g., U.S. Pat. No. 5,010,175, Furka, Pept. Prot. Res. 37:487-493 (1991), Houghton et al., Nature, 354:84-88 (1991)), peptoids (PCT Publication No. WO 91/19735), encoded peptides (PCT Publication No. WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho, et al., Science 261:1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Strategene, Corp.), peptide nucleic acid libraries (see, e.g., U.S. Pat. No. 5,539,083), antibody libraries (see, e.g., Vaughn et al., Nature Biotechnology 14(3):309-314 (1996), and PCT/US96/10287), carbohydrate libraries (see, e.g., Liang et al., Science 274:1520-1522 (1996), and U.S. Pat. No. 5,593,853), and small organic molecule libraries (see, e.g., benzodiazepines, Baum, C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. The above devices, with appropriate modification, are suitable for use with the present invention. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

For detection of interferon-receptor interactions, assays that detect IFN-mediated signal transduction may be used such as IFN-mediated inhibition of cell proliferation in cultured human tumor cell lines. Additionally, reporter gene assays may be used, for example, using reporter genes expressed from an IFN-sensitive gene promoter. Lallemand et al., J. Leukocyte Biol. 60:137-146 (1996). Suitable reporter genes include genes encoding luciferase and green fluorescent protein. In such an assay, reporter gene expression is dependent on IFN activity and the IFN antagonist selectively inhibits IFN-stimulated gene expression.

High throughput assays for evaluating the presence, absence, quantification, or other properties of particular polypeptides are well known to those of skill in the art. Similarly, binding assays and reporter gene assays are similarly well known. Thus, e.g., U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate procedures, including sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

In one embodiment, modulators are proteins, often naturally occurring proteins or fragments of naturally occurring proteins. Thus, e.g., cellular extracts containing proteins, or random or directed digests of proteinaceous cellular extracts, may be used. In this way libraries of proteins may be made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes or ligands and receptors.

In a preferred embodiment, modulators are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that the nucleic acid or peptide consists of essentially random sequences of nucleotides and amino acids, respectively. Since these random peptides (or nucleic acids, discussed below) are often chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. In a preferred embodiment, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc.

Compositions Comprising Type 1 Interferon Antagonists

In additional embodiments, the present invention concerns formulation of one or more of the type 1 interferon antagonists disclosed herein in pharmaceutically-acceptable carriers for administration to a cell or an animal, either alone, or in combination with one or more other modalities of therapy. For example, depending on the particular therapeutic regimen contemplated, compositions of the present invention may further comprise one or more additional therapeutic such as, for example, an immunosuppressive, an anti-inflammatory, a steroid, an immunomodulatory agent, a cytokine, and a TNF antagonist. Exemplary immunosuppressives include azathioprine, methotrexate, cyclosporine, FK506, rapamycin, and mycophenolate mofetil. Exemplary anti-inflammatories include 5-aminosalicylic acid, sulfasalazine and olsalazine. Exemplary steroids include corticosteroids, glucocorticosteroids, prednisone, prednisolone, hydrocortisone, methylprednisolone, dexamethasone, and ACTH. Exemplary immunomodulatory agents include PVAC, anti-CD40 ligand, anti-CD40, natalizumab (Antegren™), anti-VCAM1, and anti-ICAM1. Exemplary cytokines include IL-10. Exemplary TNF antagonists include infliximab (Remicade®), etanercept (Enbrel®), adalimumab (Humira™), and CDP870.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein.

Therefore, in another aspect of the present invention, pharmaceutical compositions are provided comprising one or more of the antibody proteins and/or small molecules described herein in combination with a physiologically acceptable carrier.

It will be apparent that any of the pharmaceutical compositions described herein can contain pharmaceutically acceptable salts of the polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the compositions of this invention, the type of carrier will typically vary depending on the mode of administration. Compositions of the present invention may be formulated for any appropriate manner of administration, including for example, oral, nasal, mucosal, intravenous, intraperitoneal, and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT Publication Nos. WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in PCT Publication No. WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit Rev Ther Drug Carrier Syst 1998; 15(3):243-84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein intravenously or intramuscularly. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, the solution should be suitably buffered if necessary and the liquid diluent first rendered isotonic with sufficient saline or glucose. These particular aqueous solutions are especially suitable for intravenous and intramuscular administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2; 50(1-3):31-40; and U.S. Pat. No. 5,145,684.

Therapeutic Methods for the Treatment of Inflammatory Bowel Diseases

As indicated herein above, the present invention also provides therapeutic methods for the treatment of Inflammatory Bowel Disease such as, for example, Celiac Disease, Crohn's Disease, and ulcerative colitis, which methods comprise the step of administering to a patient afflicted with IBD, a therapeutically effective amount of a composition comprising a type 1 interferon antagonist such as, for example, one of the antibody-based type 1 interferon antagonists described herein above. The present invention also provides, within further embodiments, therapeutic methods for the treatment of Inflammatory Bowel Disease which methods comprise the steps of (a) administering to a patient afflicted with IBD, a tolerizing amount of a type 1 interferon antagonist and (b) administering to the patient a therapeutically effective amount of a type 1 interferon antagonist. Furthermore, it may be desirable to administer one or more type 1 interferon antagonists in combination with other therapeutics such as, for example, an immunosuppressive, an anti-inflammatory, a steroid, an immunomodulatory agent, a cytokine, and a TNF antagonist such as those identified herein above.

Routes and frequency of administration of the therapeutic compositions described herein, as well as dosage, will vary from individual to individual, and may be readily established using standard techniques. By the methods of the present invention, the antagonist may be administered by any suitable route of delivery so as to ensure appropriate bioavailability. Thus, within certain embodiments, suitable routes of administration may include intravenous bolus, intravenous slow bolus, or infusion. By other embodiments, administration of the type 1 interferon antagonist may be achieved through subcutaneous, intramuscular, transdermal or intradermal injection. Alternative embodiments provide that administration may be achieved through mucosal delivery such as, for example, through inhalation (e.g., by aspiration), or through nasopharyngeal or oral administration.

Within certain embodiments employing a protein antagonist, such as, for example, an antibody and/or an antigen binding fragment thereof, the route of administration may be subcutaneous, intramuscular and/or intravenous. Intravenous administration may be as a bolus injection, a slow bolus injection, or as an infusion. Alternative embodiments provide that the protein antagonists may be delivered transdermally, intradermally, and mucosally.

In general, an appropriate dosage and treatment regimen provides the active compound(s) in an amount sufficient to provide therapeutic benefit. Such a response can be monitored by establishing an improved clinical outcome (e.g., reductions in abdominal pain; bloody diarrhea; 'extra-intestinal' manifestations such as arthritis, uveitis, and skin changes, etc.; and in the accumulation of inflammatory cells within the small intestine and colon).

Depending on the precise nature of the treatment regimen, appropriate dosages of the type 1 interferon antagonists disclosed herein may be between 0.1 and 50 mg/kg body weight, inclusive, more preferably between 0.5 and 10 mg/kg body weight, inclusive, and still more preferably between 2 and 5 mg/kg body weight, inclusive. Within certain embodiments, multiple repeat doses may be administered.

Within embodiments of the present invention employing protein antagonists, the dosing frequency may be in the range of once per day to once per month, inclusive, more preferably, in the range of twice per week to every two weeks, inclusive, and still more preferably approximately once per week.

Still further embodiments of the present invention provide methods for treating a patient suffering from an Inflammatory Bowel Disease which methods comprise the steps of (a) administering a tolerizing dose of a type 1 interferon antagonist wherein the first type 1 interferon antagonist is a protein antagonist and (b) administering a therapeutically effective dose of said type 1 interferon antagonist. Within preferred embodiments of these methods, the interferon antagonist may be an antibody against the type 1 interferon receptor (IFNAR). Exemplary anti-type 1 interferon antibodies include chimeric, primatized, humanized, de-immunized and human antibodies. Certain preferred anti-IFNAR antibodies include those that bind to IFNAR 1 such as, for example, the murine monoclonal antibody designated 64G12 and/or the engineered human variant designated CPI-1697.

To achieve an initial tolerizing dose, anti-type 1 interferon antibodies may be immunogenic in humans and in non-human primates. The immune response may be biologically significant and may impair the therapeutic efficacy of the antibody even if the antibody is partly or chiefly comprised of human immunoglobulin sequences such as, for example, in the case of a chimeric, primatized, or humanized antibody. Within certain preferred embodiments, an initial high dose of antibody is administered such that a degree of immunological tolerance to the therapeutic antibody is established. The tolerizing dose is sufficient to prevent or reduce the induction of an IgG antibody response to repeat administration of the anti-IFNAR antibody.

Preferred ranges for the tolerizing dose of the first type 1 interferon antagonist are between 10 mg/kg body weight to 50 mg/kg body weight, inclusive. More preferred ranges for the tolerizing dose are between 20 and 40 mg/kg, inclusive. Still more preferred ranges for the tolerizing dose are between 20 and 25 mg/kg, inclusive.

Within these therapeutic regimens, the therapeutically effective dose of anti-type 1 interferon is preferably administered in the range of 0.1 to 10 mg/kg body weight, inclusive. More preferred second therapeutically effective doses are in the range of 0.2 to 5 mg/kg body weight, inclusive. Still more preferred therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose. Preferably the therapeutic doses are administered intravenously, intramuscularly, or subcutaneously.

The following Example is offered by way of illustration and not by way of limitation.

EXAMPLE

Use of IFNAR-1 Antagonist in the Treatment of Inflammatory Bowel Disease

Idiopathic colitis in the cotton-top tamarin (CTT; *Sanguinus oedipus*), a new-world primate species, is recognized in the art as a model of Inflammatory Bowel Disease (IBD) in humans. Afflicted animals have a similar pathophysiology to ulcerative colitis, with similar histological changes observed to the colon, and a common sequela in humans and CTT is colon cancer. Colitis in CTT is associated with morbidity and mortality, both in the colitis phase and due to the colon cancer. The colitis is characterized by repetitive outbreaks of symptoms, with remission. Disease periods generally last about 4 weeks, although there is significant individual variability. The clinical symptoms include diarrhea with blood in feces, with a maldigestion/malabsorption syndrome. Histologically, the disease is characterized by infiltration of neutrophils into the mucosal epithelium of the large intestine, with progressive degenerative changes to the morphology of the intestinal crypts, which enable diagnosis of stage of progression of the disease. While the cause is not known, dietary and infectious agents probably have a role and almost certainly lead to exacerbation of the condition.

An engineered humanized from of the mouse 64G12 antibody, CPI-1697, (IgG4k), has been developed, which binds IFNAR1 and competes with 64G12 for binding to a similar epitope. CPI-1697 was used to treat idiopathic colitis in CTT as follows. Experimentally naïve animals were selected from a colony, on the basis of a history of colitis and exhibiting clinical symptoms including diarrhea and weight loss at the time of entry into the study. Animals underwent colon biopsy, confirming inflammation of the colon within two weeks prior to initiation of the experiment. All study animals had positive histological colitis scores of 2, in a range of 0-4, (0=normal tissue) for activity, hyperplasia and chronicity, according to an established quantification scheme. Madara et al., Gastroenterology 88:13-19 (1985)). Animals were prescreened for IFNAR-1 levels prior to inclusion in the study by flow cytometry, using phycoerythrin-conjugated CPI-1697 on isolated peripheral blood leucocytes. CPI-1697 was sterile-filtered and prepared at 20 mg/mL in vehicle solution (Dulbecco's Na PBS (sterile, USP).

The experiment was conducted in two sequential phases. In the first experiment (Phase I), 5 animals with colitis were treated with an initial dose of CPI-1697 at 20 mg/kg, given by slow i.v. infusion, followed by seven 10 mg/kg doses administered i.m. twice weekly for 4 weeks. Five control animals were administered equivalent volumes of vehicle solution (Dulbecco's Na PBS) according to the same dosing schedule. In the second experiment (Phase II), 6 animals were treated with CPI-1697 under the same initial i.v. dose (20 mg/kg) followed by twice-weekly i.m. doses (10 mg/kg) for 8 weeks. 5 control animals were administered vehicle solution according to the same schedule. In both phases, animals were monitored for body weight (twice weekly), diarrhea and periodically by histologic scoring of colon biopsy.

In Phase I, animals were assessed both during the time of treatment and then followed for 6 weeks after the end of the treatment period, and for 4 weeks after the end of treatment in Phase II. All animals were also followed-up further on weights and colon histology at 51 weeks and 27 weeks after the end of treatment for Phase I and II, respectively. Diarrhea was graded and scored visually at least 5 times per week based on a standardized 0-5 scale, where 0 represented normal fecal stools, and 5 represented very watery diarrhea. Venous blood samples were taken at regular intervals for analysis of primate anti-human antibody immune responses (PAHA). Colon biopsies were taken at three sites (1, 3 and 6 cm from the distal end of the colon) at intervals during the treatment and follow-up period, and the tissue was fixed in formalin, sectioned and stained with hematoxylin and eosin for histologic evaluation.

The sections were scored by a veterinary histopathologist, who was blinded to the treatment groups. The scoring system, from 0 (normal) to 4 (severe), used 3 independent criteria as follows (Madara et al., 1985). The first parameter was "activity"—number of infiltrating neutrophils, the second was "chronicity"—extent of permanent changes to the colon morphology, including loss of crypts and alterations in glandular structures, which characteristically slowly increase over the duration of the course of colitis, and the third was "hyperplasia'—abnormal increase in mucosal tissue thickness, including cellular and interstitial tissue. A mean histology score was determined from the three biopsy levels, for each of the 3 parameters assessed, at each time point.

Body weights for Phase I and Phase II are shown in FIGS. 1A-1D and 2A-2D, respectively. Diarrhea scores for Phase I and Phase II are shown in FIGS. 3A-3D and 4A-4D, respectively. "Activity" scores for Phase I and Phase II are shown in FIGS. 5A-5D and 6A-6D, respectively. "Chronicity" scores for Phase I and Phase II are shown in FIGS. 7A-7D and 8A-8D, respectively. "Hyperplasia" scores for Phase I and Phase II are shown in FIGS. 9A-9D and 10A-10D, respectively.

One animal (#25285) in the control group of Phase I was euthanized during the treatment period for an increased inguinal hernia unrelated to ulcerative colitis or treatment regime. No animal died in the treated group of Phase I. For Phase II, both the control and treated groups had one animal die during the treatment period. Of the surviving animals, the treated group had a bigger percentage body weight increase than the control group in both Phase I and Phase II study throughout the study period (FIGS. 1A-1D and 2A-2D). The body weight increase was most prominent 4 to 6 weeks after the end of dosing period. Most interestingly, long-term follow-up on the animals until 51 weeks after the dosing period for Phase I study and 27 or 43 weeks for Phase II study showed even bigger body weight percent increase in the treated animals compared with the control animals. In particular, Phase I treated animals had statistically significant body weight percent increase over the controls ($p<0.01$). Three animals (#4199, 12300, 52099) in the treated group showing good body weight increase were found out to be under 20 month at the initiation of the study and the body weight increase could be due to normal growth of young animals.

The effect of CPI-1697 treatment on diarrhea scores of CTT is summarized in FIGS. 3A-3D and 4A-4D. The group mean weekly average diarrhea score showed an improvement (decrease in score) in the treated group during the course of the study in Phase II study whereas the control group showed no improvement (FIGS. 4A-4D). The improvements in diarrhea scores started right after onset of treatment and tended to be sustained after the cessation of treatment in Phase II study. For Phase I study, the improvement in diarrhea scores was not obvious for the treatment (FIGS. 3A-3D).

The effect of CPI-1697 treatment on "activity" scores representing neutrophil infiltration in colon of CTT is summarized in FIGS. 5A-5D and 6A-6D. In Phase I study (FIGS. 5A-5D), both the control and treated group had decreased neutrophil infiltration right after initiation of study. The treated group had increased neutrophil infiltration over the period of Week 0 to Week 8 and substantially decreased neutrophil infiltration from Week 8 to Week 10. In contrast, the control group had slightly decreased neutrophil infiltration over Week 0 to Week 10. However, by Week 55, the treated group had slightly less neutrophil infiltration than the control group. In Phase II study (FIGS. 6A-6D), the treated group had decreased neutrophil infiltration (group mean) over the 12 week study period and further reduction by Week 35 whereas the control group showed no decrease.

The effect of CPI-1697 treatment on "chronicity" scores representing extent of permanent changes to the colon morphology, including loss of crypts and alterations in glandular structures of CTT is summarized in FIGS. 7A-7D and 8A-8D. In Phase I study (FIGS. 7A-7D), both the control and treated group had improved colon morphology right after initiation of treatment, however such improvement was not sustained. The treated group did not have any additional beneficial effect on colon morphology over the control group. In Phase II study (FIGS. 8A-8D), the treated group had improved colon morphology two weeks after initiation of dosing, exactly the opposite of the control group. Moreover, the treated group had more improvement in colon morphology than the control group long term at Week 35 compared to Week 12.

The effect of CPI-1697 treatment on "hyperplasia" scores representing abnormal increase in mucosal tissue thickness, including cellular and interstitial tissue of CTT is summarized in FIGS. 9A-9D and 10A-10D. In Phase I study (FIGS. 9A-9D), similar to colon morphology change, both the control and treated group had decreased mucosal tissue thickness right after initiation of treatment, however such improvement was not sustained. The treated group did not have any additional beneficial effect on mucosal tissue thickness over the control group. In Phase II study (FIGS. 10A-10D), the treated group had similar changes as the control group in mucosal tissue thickness over the study period of 12 weeks. However, long-term follow-up showed that the treated group had decreased mucosal tissue thickness compared to the control group long term at Week 35.

Figure 11A:
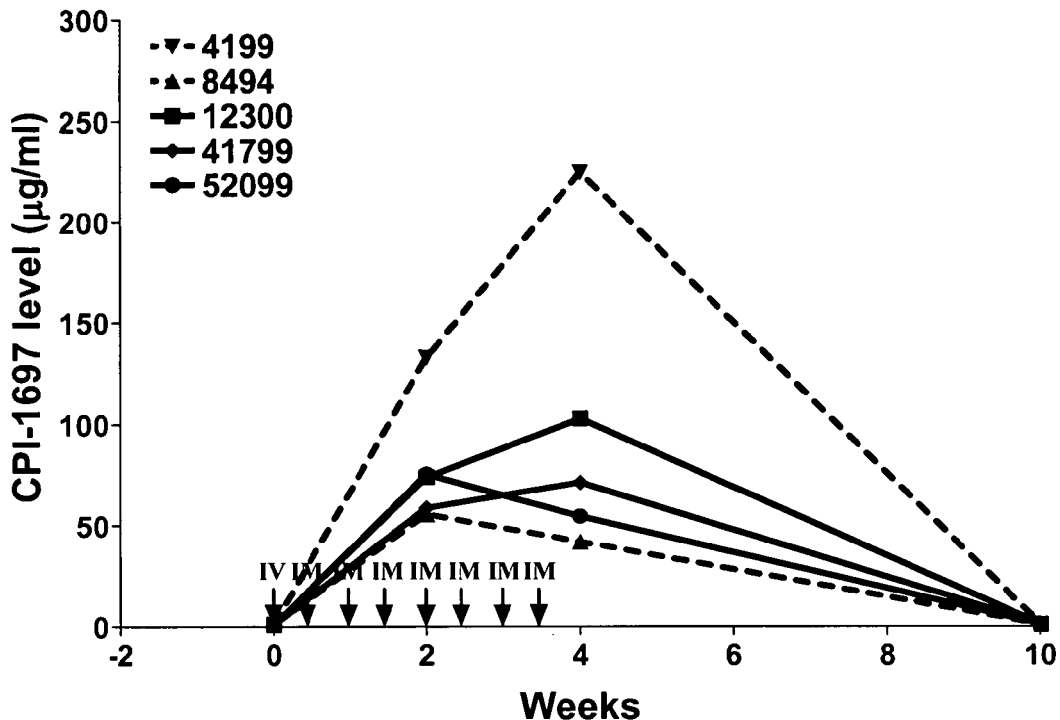
FIGS. 11A-11B are graphs showing serum CPI-1697 drug levels of individual animals in Phase I (FIG. 11A) and Phase II (FIG. 11B) studies.
Figure 11B:
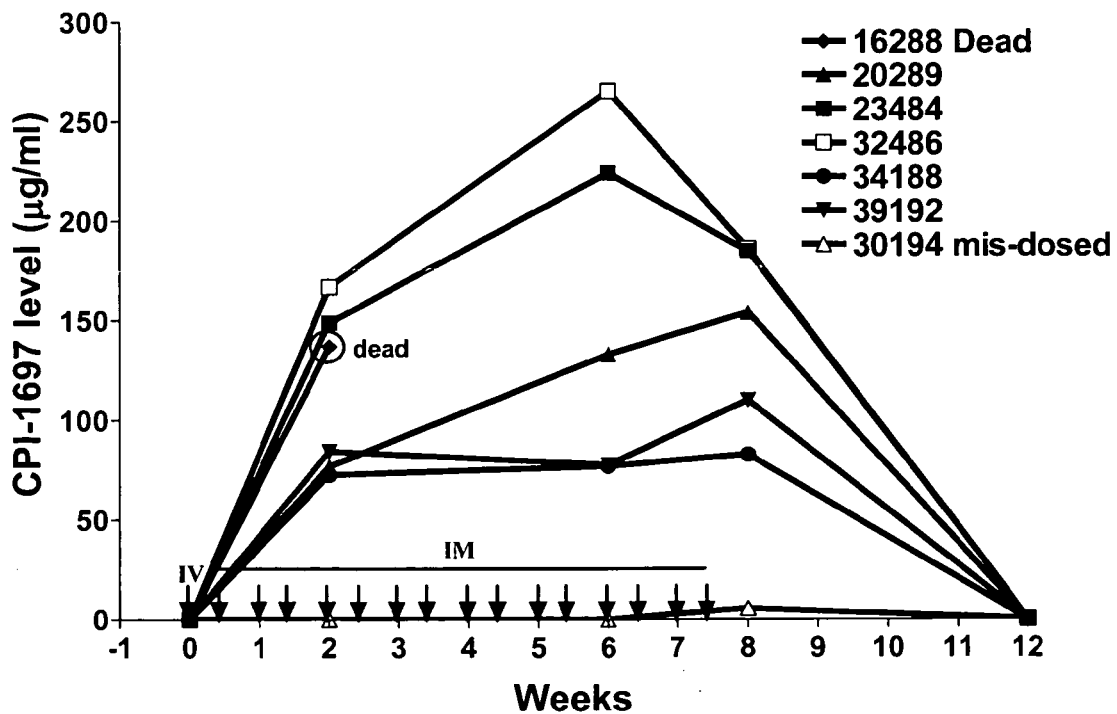
Figure 12A:
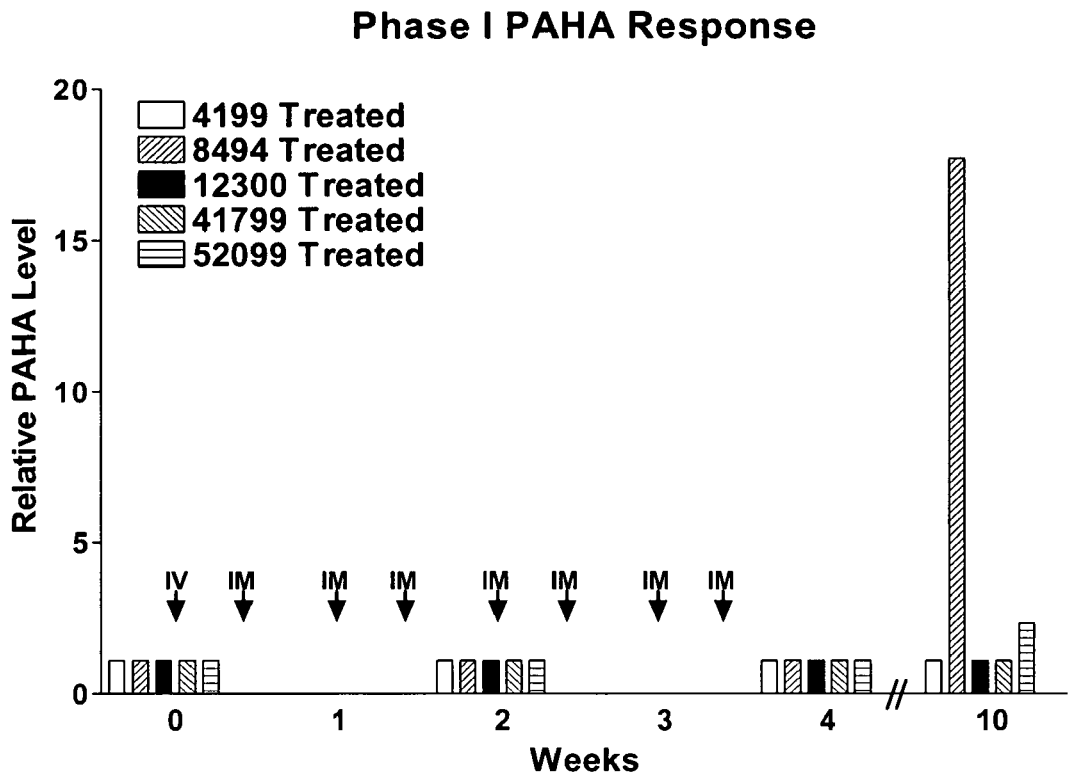
FIGS. 12A-12B are bar graphs showing relative PAHA response levels of CPI-1697 treated animals in Phase I (FIG. 12A) and Phase II (FIG. 12B) studies.
Figure 12B:
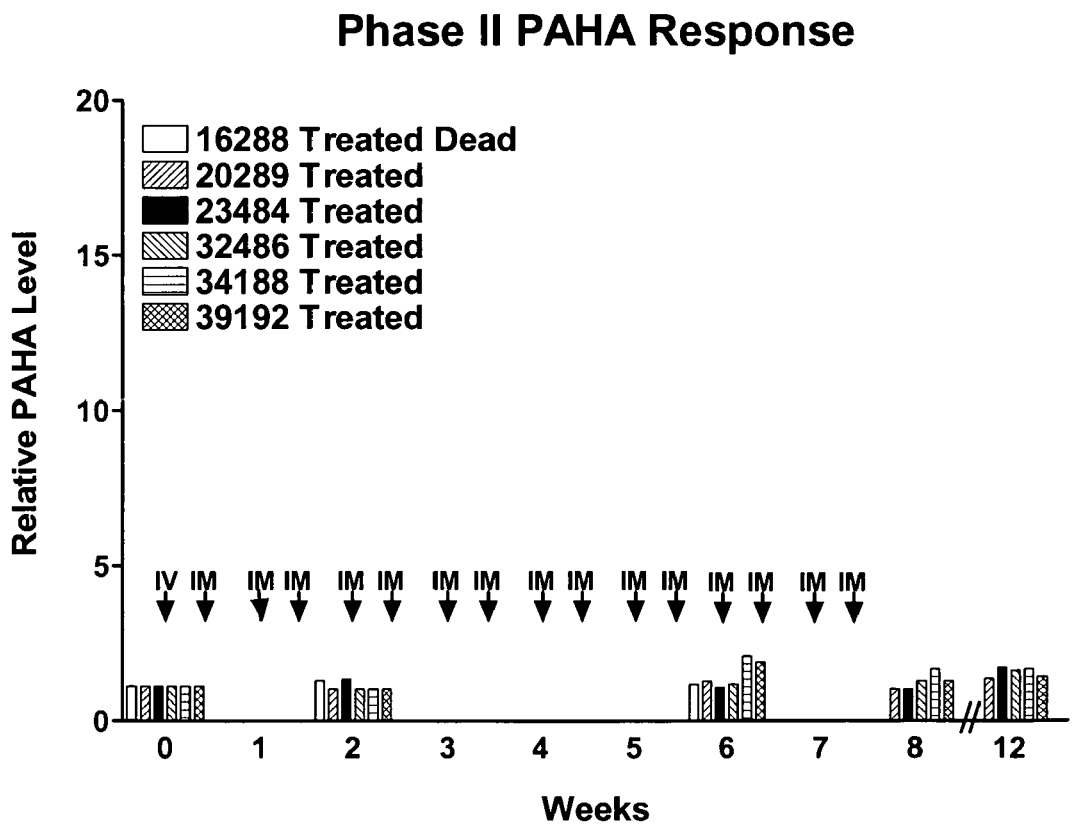

Serum samples from each animal were assayed by ELISA for levels of drug (CPI-1697 anti-IFNAR-1 antibody) by detecting human IgG4, and for primate-anti-human-antibody (PAHA) responses. As shown in FIGS. 11A-11B, drug levels of about 50-270 ng/ml of plasma were maintained throughout the treatment phase and PAHA levels were low or undetectable in the majority of animals (FIGS. 12A-12B). Although all animals received the same dose on a weight basis, certain animals were observed to have higher circulating levels of CPI-1697, of up to 3 times higher. This range of concentrations of CPI-1697 has been demonstrated previously to be effective in blocking IFNAR-1 in vitro in primate studies. Two animals (#8494 and #52099) in Phase I developed detectable PAHA responses and no detectable PAHA response was observed in any of the animals in Phase II (FIGS. 12A-12B). These results suggest that the dosing regimen used, including a high initial dose of CPI-1697 did not lead to a significant immunological response to this protein (human antibody). Those two animals also had low drug levels (FIGS. 11A-11B).

Figure 13:
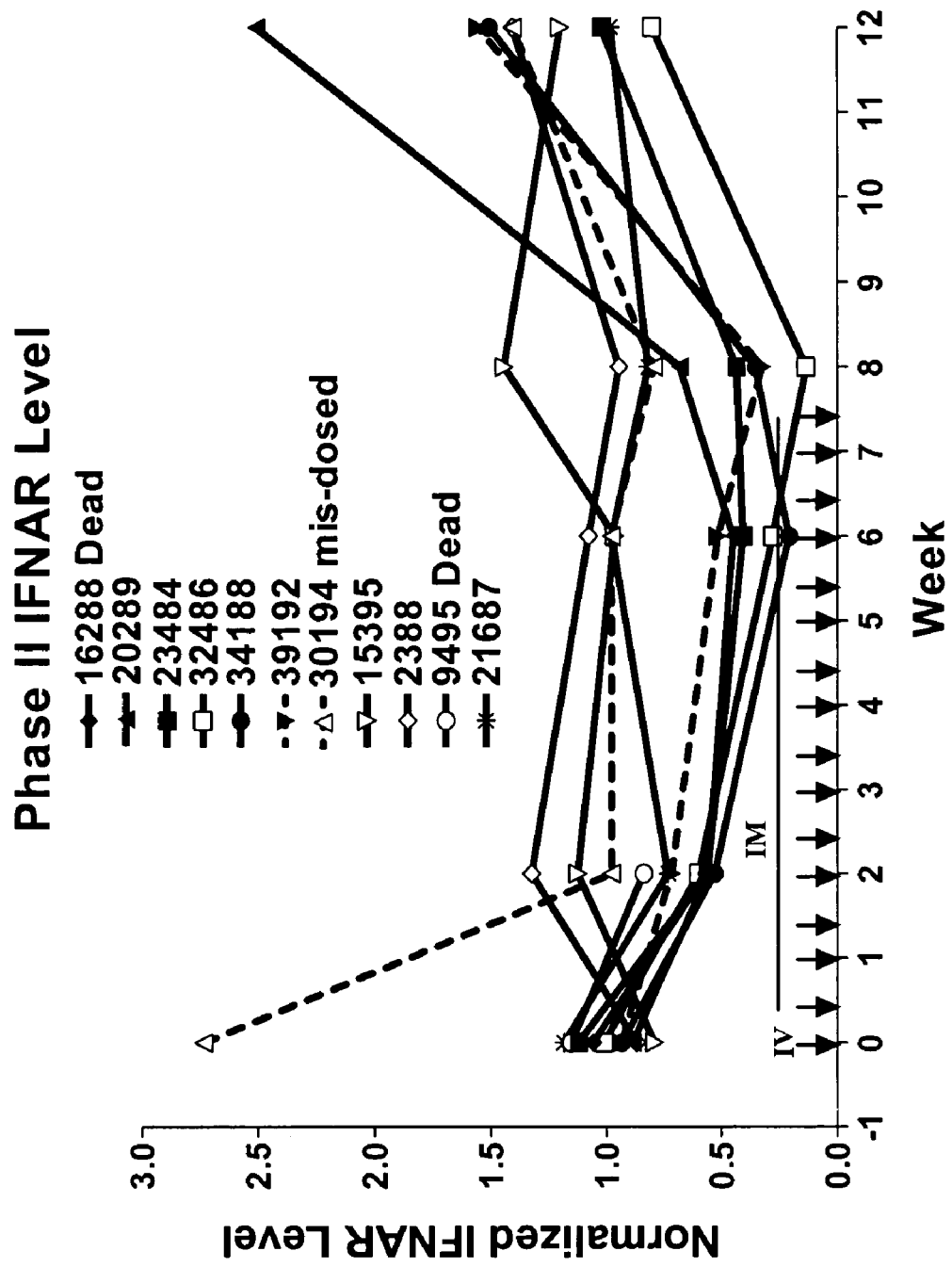
FIG. 13 is a graph showing normalized IFNAR1 expression levels on B cells of individual animals in the Phase II study. IFNAR1 expression levels on B cells of individual animals at various time-points were normalized by the mean IFNAR1 levels of the control animals at each time-point with the assumption that IFNAR1 levels remained relatively stable on control animals.

Levels of IFNAR1 on white blood cells were assayed by flow cytometry and the normalized receptor levels of Phase II study were summarized in FIG. 13. Receptor levels of Phase I study were not obtained as the FACS assays were not optimized then. Interferon receptor blocking was achieved to various levels, although not complete, in the treated animals. Animals having higher levels of serum CPI-1697 tended to have better receptor blocking.

In summary, in both Phase I and Phase II studies, CPI-1697 treatment generated weight increase benefit over control in colitis-afflicted tamarins. Phase II study with longer CPI-1697 treatment period had even better effect with improvement in diarrhea scores and histopathology scores including "activity", "chronicity" and "hyperplasia". In Phase II study, there was a correlation between positive clinical response and higher circulating levels of CPI-1697. There was also a positive correlation between lack of PAHA response and improved clinical scores. Such correlations were not found for Phase I study. These correlations were not testable by statistical methods due to the small sample size in the study. Overall these results indicate that treatment with a humanized antibody to IFNAR-1 produces a clinical improvement in colitic CTT. The effect was chronic rather than acute and trended to be sustained beyond the treatment phases, as shown by long-term follow-up study. Longer-term treatment in Phase II study produced stronger effects than shorter treatments. Increased exposure, both in time and plasma levels, to CPI-1697 was associated with greater response.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. A method for the treatment of a patient afflicted with ulcerative colitis comprising the step of administering to said patient a therapeutically effective amount of a humanized or fully human anti-type 1 interferon receptor monoclonal antibody, wherein the antibody inhibits the binding of IFN-α, IFN-β, and IFN-ω to the type 1 interferon receptor.

2. A method for the treatment of a patient afflicted with ulcerative colitis or Crohn's disease comprising the step of administering to said patient a therapeutically effective amount of a humanized or fully human anti-type 1 interferon receptor monoclonal antibody, wherein the antibody inhibits the binding of IFN-α, IFN-β and IFN-ω to the type 1 interferon receptor, and is not administered in combination with another antibody, and wherein administration of the anti-type 1 interferon receptor antibody results in decreased neutrophil infiltration as compared to a control, following administration of the anti-type 1 interferon receptor antibody.

3. A method for the treatment of a patient afflicted with ulcerative colitis or Crohn's disease comprising the step of administering to said patient a therapeutically effective amount of a humanized or fully human anti-type 1 interferon receptor monoclonal antibody, wherein the antibody inhibits the binding of IFN-α, IFN-β, and IFN-ω to the type 1 interferon receptor, and is not administered in combination with another antibody, and wherein administration of the anti-type 1 interferon receptor antibody results in improved colon morphology as compared to a control, following administration of the anti-type 1 interferon receptor antibody.

4. A method for the treatment of a patient afflicted with ulcerative colitis or Crohn's disease comprising the step of administering to said patient a therapeutically effective amount of a humanized or fully human anti-type 1 interferon receptor monoclonal antibody, wherein the antibody inhibits the binding of IFN-α, IFN-β, and IFN-ω to the type 1 interferon receptor, and is not administered in combination with another antibody, and wherein administration of the anti-type 1 interferon receptor antibody results in decreased mucosal tissue thickness as compared to a control, following administration of the anti-type 1 interferon receptor antibody.

5. A method increasing body weight in a patient afflicted with ulcerative colitis or Crohn's disease comprising the step of administering to said patient a therapeutically effective amount of a humanized or fully human anti-type 1 interferon receptor monoclonal antibody, wherein the antibody inhibits the binding of IFN-α, IFN-β, and IFN-ω the type 1 interferon receptor, and is not administered in combination with another antibody, and wherein administration of the anti-type 1 interferon receptor antibody results in measurable body weight increase as compared to a control, following administration of the anti-type 1 interferon receptor antibody.

6. A method for the treatment of a patient afflicted with ulcerative colitis or Crohn's disease comprising the step of administering to said patient a therapeutically effective amount of a humanized or fully human anti-type 1 interferon receptor monoclonal antibody, wherein the antibody inhibits the binding of IFN-α, IFN-β, and IFN-ω to the type 1 interferon receptor, and is not administered in combination with another antibody.

7. A method for the treatment of a patient afflicted with Crohn's disease comprising the step of administering to said patient a therapeutically effective amount of a humanized or fully human anti-type 1 interferon receptor monoclonal antibody, wherein the antibody inhibits the binding of IFN-α, IFN-β, and IFN-ω to the type 1 receptor, and is not administered in combination with another antibody.

8. The method of any one of claims 1, 6, and 7, wherein said anti-type 1 interferon receptor antibody is administered by a route selected from the group consisting of intravenous bolus, intravenous slow bolus, and infusion.

9. The method of any one of claims 1, 6, and 7, wherein said anti-type 1 interferon receptor antibody is administered by a route selected from the group consisting of subcutaneously, intramuscularly, transdermally, intradermally, and intravenously.

10. The method of any one of claims 1, 6, and 7, wherein said anti-type 1 interferon receptor antibody is administered in a dosage range of between 0.1 mg/kg body weight and 50 mg/kg body weight, inclusive.

11. The method of claim 10 wherein said anti-type 1 interferon receptor antibody is administered in a dosage range of between 0.5 mg/kg body weight and 10 mg/kg body weight, inclusive.

12. The method of claim 11 wherein said anti-type 1 interferon receptor antibody is administered in a dosage range of between 2 mg/kg body weight and 5 mg/kg body weight, inclusive.

13. The method of any one of claims 1, 6, and 7, wherein said anti-type 1 interferon receptor antibody is administered at a frequency between once per day and once per month, inclusive.

14. The method of claim 13 wherein said anti-type 1 interferon receptor antibody is administered at a frequency between twice per week and every two weeks, inclusive.

15. The method of claim 13 wherein said anti-type 1 interferon receptor antibody is administered at a frequency of approximately once per week.

16. The method of any one of claims 1, 6, and 7, further comprising administration of a second therapeutic selected from the group consisting of an immunosuppressive, an anti-inflammatory, a steroid, an immunomodulatory agent, a cytokine, and a TNF antagonist.

* * * * *

UNITED STATES PATENT AND TRADEMARK OFFICE
CERTIFICATE OF CORRECTION

PATENT NO. : 7,939,076 B2  
APPLICATION NO. : 10/831432  
DATED : May 10, 2011  
INVENTOR(S) : Lesley B. Pickford et al.

It is certified that error appears in the above-identified patent and that said Letters Patent is hereby corrected as shown below:

At column 25, line 62:

"A method increasing" should read --A method for increasing--

At column 25, line 67:

"IFN-ω the type 1 interferon receptor" should read --IFN-ω to the type 1 interferon receptor--

Signed and Sealed this
Twenty-fifth Day of October, 2011

David J. Kappos  
*Director of the United States Patent and Trademark Office*

UNITED STATES PATENT AND TRADEMARK OFFICE
CERTIFICATE OF CORRECTION

PATENT NO. : 7,939,076 B2  Page 1 of 1
APPLICATION NO. : 10/831432
DATED : May 10, 2011
INVENTOR(S) : Lesley B. Pickford et al.

It is certified that error appears in the above-identified patent and that said Letters Patent is hereby corrected as shown below:

At column 26, line 36:

"type 1 receptor" should read --type 1 interferon receptor--

Signed and Sealed this
Twenty-ninth Day of November, 2011

David J. Kappos
*Director of the United States Patent and Trademark Office*

SEQUENCE LISTING

```
<160> NUMBER OF SEQ ID NOS: 2

<210> SEQ ID NO 1
<211> LENGTH: 119
<212> TYPE: PRT
<213> ORGANISM: Artificial
<220> FEATURE:
<223> OTHER INFORMATION: Composite human and murine sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Phe Ser Gly Phe Thr Leu Ser Thr Ser
            20                  25                  30

Gly Met Gly Ile Gly Trp Val Arg Gln Ala Pro Gly Lys Gly Leu Glu
        35                  40                  45

Trp Val Ala His Trp Trp Asp Asp Lys Tyr Tyr Asn Pro Ser Leu
    50                  55                  60

Lys Ser Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asn Tyr Tyr Pro Tyr Asp Ala Trp Phe Asp Tyr Trp Gly Gln
            100                 105                 110

Gly Thr Leu Val Thr Val Ser
        115

<210> SEQ ID NO 2
<211> LENGTH: 109
<212> TYPE: PRT
<213> ORGANISM: Artificial
<220> FEATURE:
<223> OTHER INFORMATION: Composite human and murine sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Asn Ser Asn
            20                  25                  30
```

```
His Leu His Trp Tyr Gln Gln Lys Pro Gly Lys Ala Pro Lys Leu Leu
        35              40              45

Ile Tyr Arg Thr Ser Ile Leu Ala Ser Gly Val Pro Ser Arg Phe Ser
    50              55              60

Gly Ser Gly Ser Gly Thr Ser Phe Thr Leu Thr Ile Ser Ser Leu Gln
65              70              75                  80

Pro Glu Asp Phe Ala Thr Tyr Tyr Cys Gln Gln Gly Ser Asn Ile Pro
            85              90              95

Phe Thr Phe Gly Gln Gly Thr Lys Val Glu Ile Lys Arg
            100             105
```